(12) United States Patent
Schmidt et al.

(10) Patent No.: US 7,816,304 B2
(45) Date of Patent: *Oct. 19, 2010

(54) MASS LABELS

(75) Inventors: Gunter Schmidt, Houghton (GB); Andrew Hugin Thompson, Alloway (GB); Robert Alexander Walker Johnstone, Bebington (GB)

(73) Assignee: Electrophoretics Limited, Cobham (GB)

( * ) Notice: Subject to any disclaimer, the term of this patent is extended or adjusted under 35 U.S.C. 154(b) by 377 days.

This patent is subject to a terminal disclaimer.

(21) Appl. No.: 11/841,707

(22) Filed: Aug. 20, 2007

(65) Prior Publication Data

US 2008/0167197 A1    Jul. 10, 2008

Related U.S. Application Data

(62) Division of application No. 10/221,666, filed as application No. PCT/GB01/01122 on Mar. 14, 2001, now Pat. No. 7,294,456.

(30) Foreign Application Priority Data

Mar. 14, 2000   (GB) ................. 0006141.6

(51) Int. Cl.
 *C40B 40/00*   (2006.01)
(52) U.S. Cl. ................. 506/13; 506/7; 506/23; 435/6
(58) Field of Classification Search ........... None
See application file for complete search history.

(56) References Cited

U.S. PATENT DOCUMENTS

| | | | |
|---|---|---|---|
| 5,705,610 A | 1/1998 | Zuckermann et al. |
| 5,800,992 A | 9/1998 | Fodor et al. |
| 6,027,890 A | 2/2000 | Ness et al. |
| 6,824,981 B2 | 11/2004 | Chait et al. |

FOREIGN PATENT DOCUMENTS

| | | |
|---|---|---|
| JP | 8-145948 A | 6/1996 |
| WO | WO97/37041 | 10/1997 |
| WO | WO 97/37953 | 10/1997 |
| WO | WO98/15652 | 4/1998 |
| WO | WO98/31830 | 7/1998 |
| WO | WO 98/31830 A1 | 7/1998 |
| WO | WO 99/02728 | 1/1999 |
| WO | WO99/02728 | 1/1999 |
| WO | WO99/13103 | 3/1999 |
| WO | WO99/14362 | 3/1999 |
| WO | WO 99/32501 | 7/1999 |
| WO | WO 00/02895 A1 | 1/2000 |

OTHER PUBLICATIONS

Dunayevskiy, Yuriy et al., "Application of capillary electrophoresis-electrospray ionization mass spectrometry in the determination of molecular diversity" Proc. Natl. Acad. Sci. USA, vol. 93, pp. 6152-6157, Jun. 1996.

Kim et al., "Specific Association of Human Telomerase Activity with Immortal Cells and Cancer," Science, vol. 266 (Dec. 23, 1994), pp. 2011-2015.

Broccoli et al., "Telomerase Activity in Normal and Malignant Hematopoietic Cells," Proc. Natl. Acad. Sci. USA, vol. 92 (Sep. 1995), pp. 9082-9086.

English translation of Japanese Office Action dated Oct. 13, 2009 (Three (3) pages).

*Primary Examiner*—Jeffrey S. Lundgren
(74) *Attorney, Agent, or Firm*—Crowell & Moring LLP

(57) ABSTRACT

Provided herein are sets of mass labels. Each mass label in a set includes: 1) a mass marker moiety; 2) a mass normalisation moiety; and 3) a cleavable linker connecting the mass marker moiety to the mass normalisation moiety. Each mass marker moiety is characterized as having a mass different from that of all other mass marker moieties in the set as determined by mass spectrometry. Further, each mass normalization moiety ensures that each mass label in the set has substantially the same mass as determined by mass spectrometry.

71 Claims, 15 Drawing Sheets

Q1 cycles rapidly round these masses continuously

Oligos generated after attachment of mixture of mass labels

Oligo A ——— $aM_0X_3$

Oligo A ——— $bM_1X_2$

Oligo A ——— $cM_2X_1$

Oligo A ——— $dM_3X_0$

Detection of oligo in Q3 m/z

Full Mass Spectrum:

Mass Spectrum 1

Selective Mass Spectrum:

Mass Spectrum 2

Mass Spectrum 3:
$A_1^+$ mass spectrum

Mass Spectrum 4:
$A_2^+$ mass spectrum

Mass Spectrum 5

Selected Reaction Product Identifies Analyte

Mass Spectrum 6

Mass Spectrum 7

Mass Spectrum 8

MASS LABELS

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The present application constitutes a divisional application of U.S. patent application Ser. No. 10/221,666, filed Feb. 13, 2003, now U.S. Pat. No. 7,294,456, which claims priority to international application serial no. PCT/GB01/01122, filed Mar. 14, 2001, which claims priority to foreign application serial no. GB0006141.6, filed Mar. 14, 2000. Each of these prior applications is hereby incorporated by reference in its entirety.

This invention relates to useful compounds for labelling analytes, particularly biomolecules such as nucleic acids and proteins. Specifically this invention relates to methods of analysis by mass spectrometry, using specific mass labels.

Various methods of labelling molecules of interest are known in the art, including radioactive atoms, fluorescent dyes, luminescent reagents, electron capture reagents and light absorbing dyes. Each of these labelling systems has features which make it suitable for certain applications and not others. For reasons of safety, interest in non-radioactive labelling systems has lead to the widespread commercial development of fluorescent labelling schemes particularly for genetic analysis. Fluorescent labelling schemes permit the labelling of a relatively small number of molecules simultaneously, typically four labels can be used simultaneously and possibly up to eight. However the costs of the detection apparatus and the difficulties of analysing the resultant signals limit the number of labels that can be used simultaneously in a fluorescence detection scheme.

More recently there has been development in the area of mass spectrometry as a method of detecting labels that are cleavably attached to their associated molecule of interest. In many molecular biology applications one needs to be able to separate the molecules of interest prior to analysis. Generally, liquid phase separations are performed. Mass spectrometry in recent years has developed a number of interfaces for liquid phase separations, which make mass spectrometry particularly effective as a detection system for these kinds of applications. Until recently Liquid Chromatography Mass Spectrometry was used to detect analyte ions or their fragment ions directly. However, for many applications such as nucleic acid analysis, the structure of the analyte can be determined from indirect labelling. This is advantageous particularly with respect to the use of mass spectrometry because complex biomolecules such as DNA have complex mass spectra and are detected with relatively poor sensitivity. Indirect detection means that an associated label molecule can be used to identify the original analyte, the label being designed for sensitive detection and having a simple mass spectrum. Simple mass spectra allow multiple labels to be used to analyse a plurality of analytes simultaneously.

PCT/GB98/00127 describes arrays of nucleic acid probes covalently attached to cleavable labels that are detectable by mass spectrometry, which identify the sequence of the covalently linked nucleic acid probe. The labelled probes of this application have the structure Nu-L-M where Nu is a nucleic acid covalently linked to L, a cleavable linker, covalently linked to M, a mass label. Preferred cleavable linkers in this application cleave within the ion source of the mass spectrometer. Preferred mass labels are substituted poly-aryl ethers. This application discloses a variety of ionisation methods, and analysis by quadrupole mass analysers, time of flight (TOF) analysers and magnetic sector instruments as specific methods of analysing mass labels by mass spectrometry.

PCT/GB94/01675 discloses ligands, and specifically nucleic acids, cleavably linked to mass tag molecules. Preferred cleavable linkers are photo-cleavable. This application discloses Matrix Assisted Laser Desorption Ionisation (MALDI) TOF mass spectrometry as a specific method of analysing mass labels by mass spectrometry.

PCT/US97/22639 discloses releasable non-volatile mass-label molecules. In preferred embodiments these labels comprise polymers, typically biopolymers which are cleavably attached to a reactive group or ligand, i.e. a probe. Preferred cleavable linkers appear to be chemically or enzymatically cleavable. This application discloses MALDI TOF mass spectrometry as a specific method of analysing mass labels by mass spectrometry.

PCT/US97/01070, PCT/US97/01046, and PCT/US97/01304 disclose ligands, and specifically nucleic acids, cleavably linked to mass tag molecules. Preferred cleavable linkers appear to be chemically or photo-cleavable. These applications disclose a variety of ionisation methods and analysis by quadrupole mass analysers, TOF analysers and magnetic sector instruments as specific methods of analysing mass labels by mass spectrometry.

The mass spectra generated for an analyte material are very sensitive to contaminants. Essentially, any material introduced into the mass spectrometer that can ionize will appear in the mass spectrum. This means that for many analyses it is necessary to carefully purify the analyte before introducing it into the mass spectrometer. For the purposes of high throughput systems for indirect analysis of analytes through mass labels it would be desirable to avoid any unnecessary sample preparation steps. That is to say it would be desirable to be able to detect labels in a background of contaminating material and be certain that the peak that is detected does in fact correspond to a label. The prior art does not disclose methods or compositions that can improve the signal to noise ratio achievable in mass spectrometry based detection systems or that can provide confirmation that a mass peak in a spectrum was caused by the presence of a mass label.

For the purposes of detection of analytes after liquid chromatography or electrophoretic separations, it is desirable that the labels used minimally interfere with the separation process. If an array of such labels are used, it is desirable that the effect of each member of the array on its associated analyte is the same as every other labels. This conflicts to some extent with the intention of mass marking which is to generate arrays of labels that are resolvable in the mass spectrometer on the basis of their mass. Mass labels should preferably be resolved by 4 daltons to prevent interference of isotope peaks from one label with those of another label. This means that to generate 250 distinct mass labels would require labels spread over a range of about 1000 daltons and probably more, since it is not trivial to generate large arrays of labels separated by exactly 4 daltons. This range of mass will almost certainly result in mass labels that will have a distinct effect on any separation process that precedes detection by mass spectrometry. It also has implications for instrument design, in that as the mass range over which a mass spectrometer can detect ions increases, the cost of the instrument increases.

It is thus an object of this invention to solve the problems associated with the above prior art, and provide mass labels which can be detected in a background of contamination and whose identity as mass labels can be confirmed. Furthermore it is an object of this invention to provide arrays of labels which can be resolved in a compressed mass range so that the labels do not interfere as much with separation processes and which can be detected easily in a mass spectrometer that detects ions over a limited range of mass to charge ratios.

It is also an object of this invention to provide methods of analysing biomolecules which exploit the labels of this invention to maximise throughput, signal to noise ratios and sensitivity of such assays, particularly in genetic analysis and more particularly 2-dimensional gel electrophoresis which is used to analyse proteins.

Furthermore the design of the mass labels disclosed below allows a simplified tandem mass spectrometer to be designed for the purposes of detecting mass labels. The first mass analyser need only select a limited number of ions whose mass is relatively low. The second mass analyser need only detect a small number of fragmentation products.

Accordingly, the present invention provides a set of two or more mass labels, each label in the set comprising a mass marker moiety attached via a cleavable linker to a mass normalisation moiety, the mass marker moiety being fragmentation resistant, wherein the aggregate mass of each label in the set may be the same or different and the mass of the mass marker moiety of each label in the set may be the same or different, and wherein in any group of labels within the set having a mass marker moiety of a common mass each label has an aggregate mass different from all other labels in that group, and wherein in any group of labels within the set having a common aggregate mass each label has a mass marker moiety having a mass different from that of all other mass marker moieties in that group, such that all of the mass labels in the set are distinguishable from each other by mass spectrometry.

The term mass marker moiety used in the present context is intended to refer to a moiety that is to be detected by mass spectrometry, whilst the term mass normalisation moiety used in the present context is intended to refer to a moiety that is not necessarily to be detected by mass spectrometry, but is present to ensure that a mass label has a desired aggregate mass. The number of labels in the set is not especially limited, provided that the set comprises a plurality of labels. However, it is preferred if the set comprises two or more, three or more, four or more, or five or more labels.

The present invention also provides an array of mass labels, comprising two or more sets of mass labels as defined above, wherein the aggregate mass of each of the mass labels in any one set is different from the aggregate mass of each of the mass labels in every other set in the array.

Further provided by the invention is a method of analysis, which method comprises detecting an analyte by identifying by mass spectrometry a mass label or a combination of mass labels unique to the analyte, wherein the mass label is a mass label from a set or an array of mass labels as defined above.

The invention will now be described in further detail by way of example only, with reference to the accompanying drawings, in which.

Figure 9:
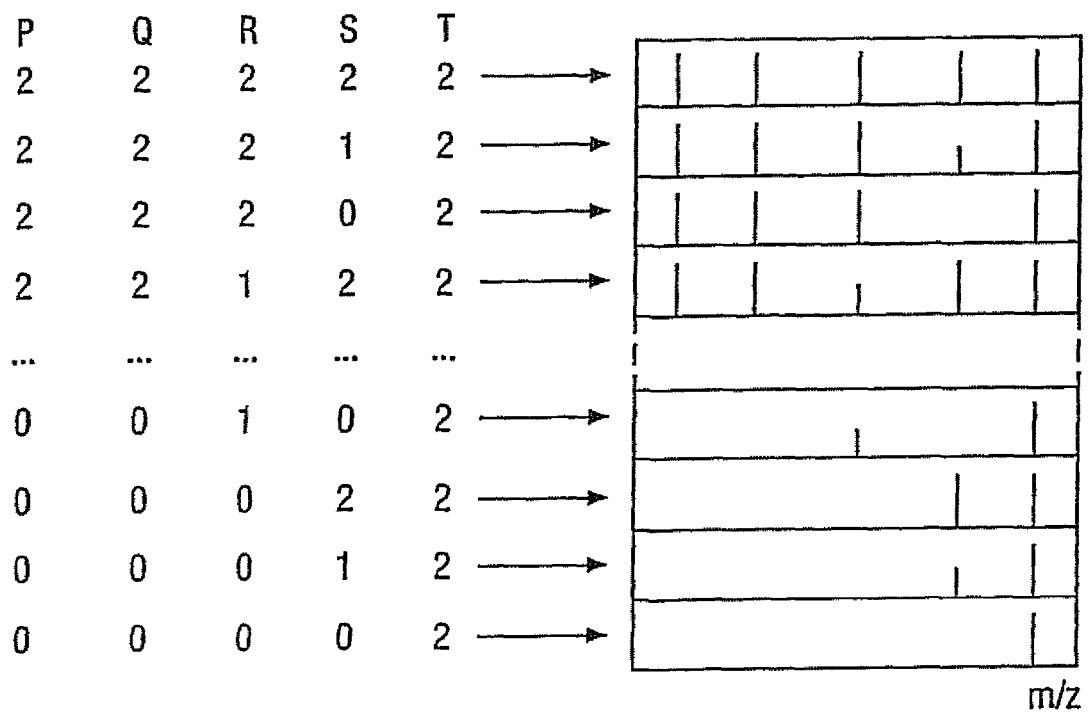
Figure 10:
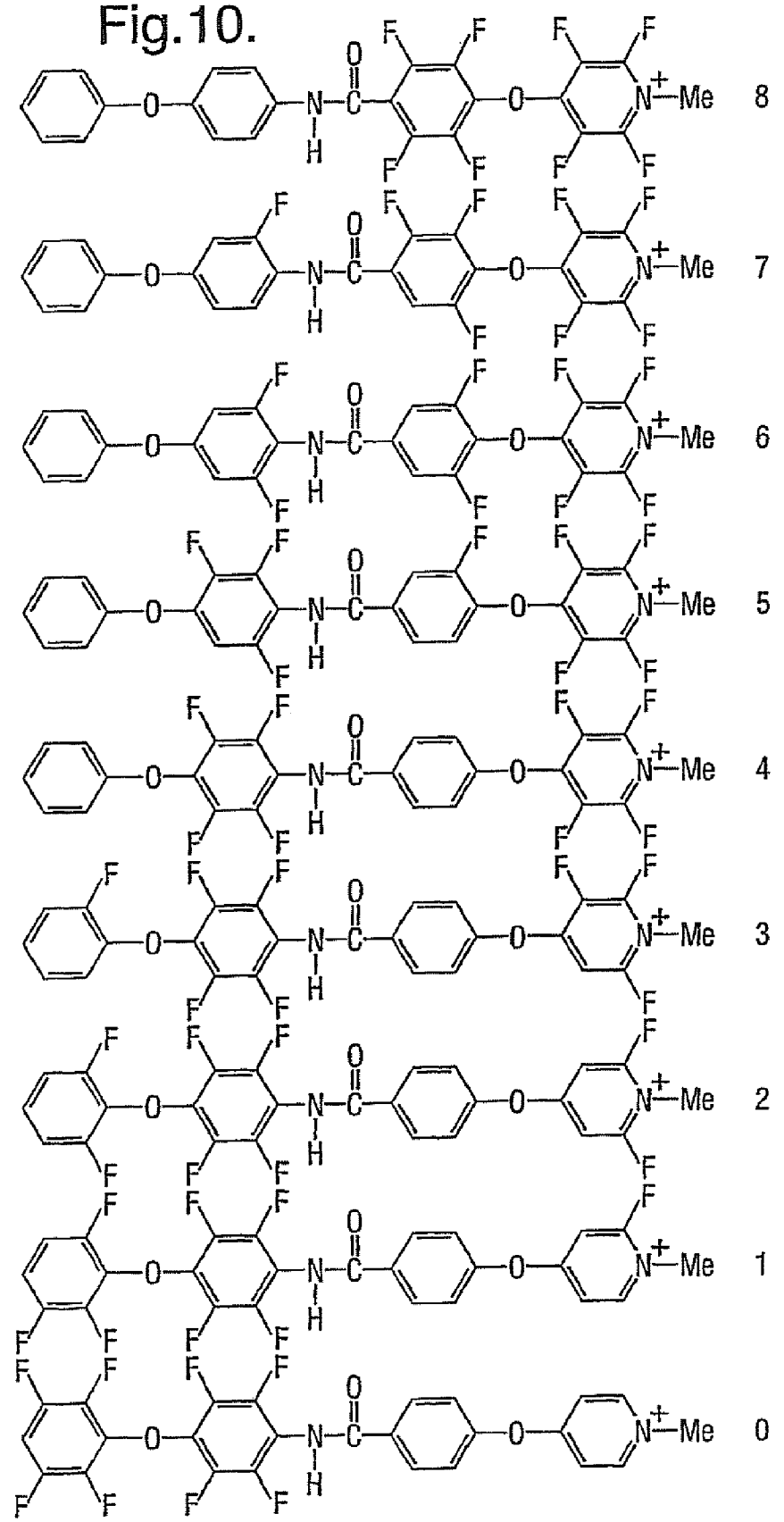
Figure 11:
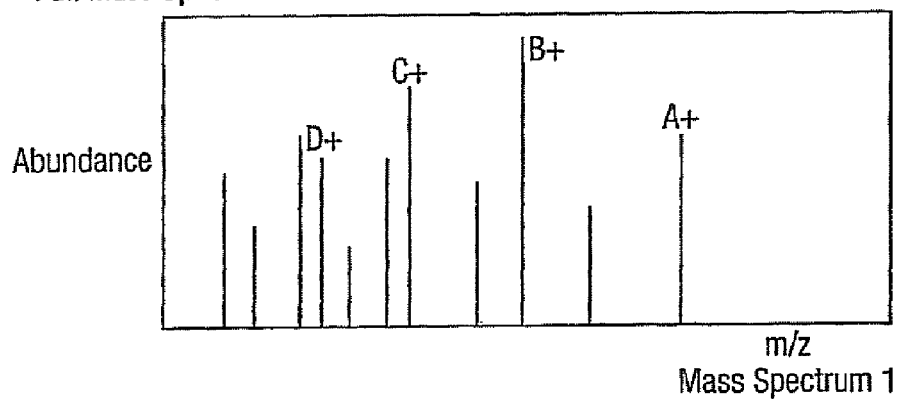
Figure 12:
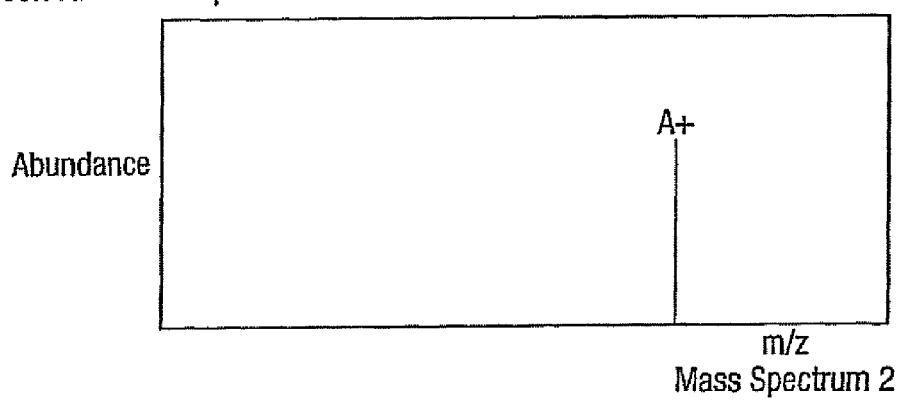
Figure 13:
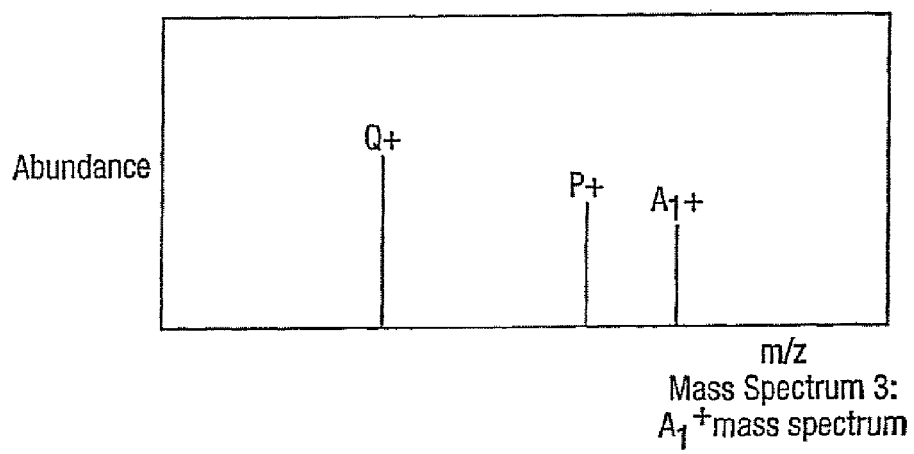
Figure 14:
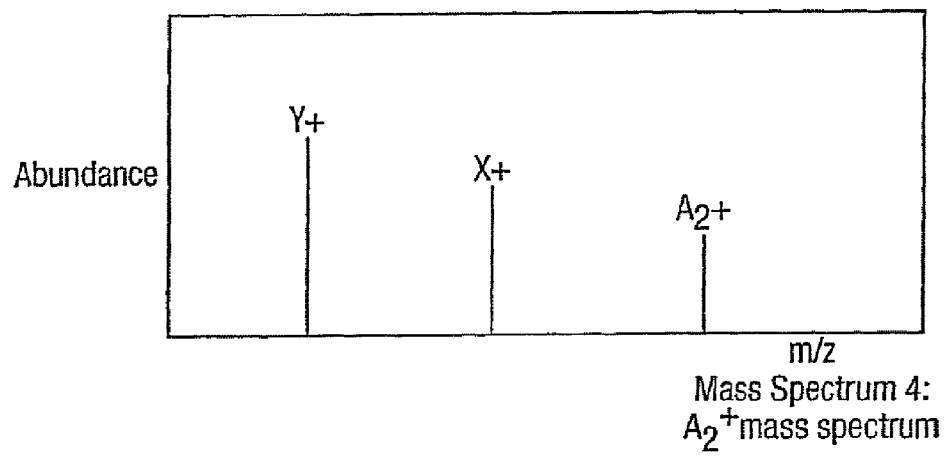
Figure 15:
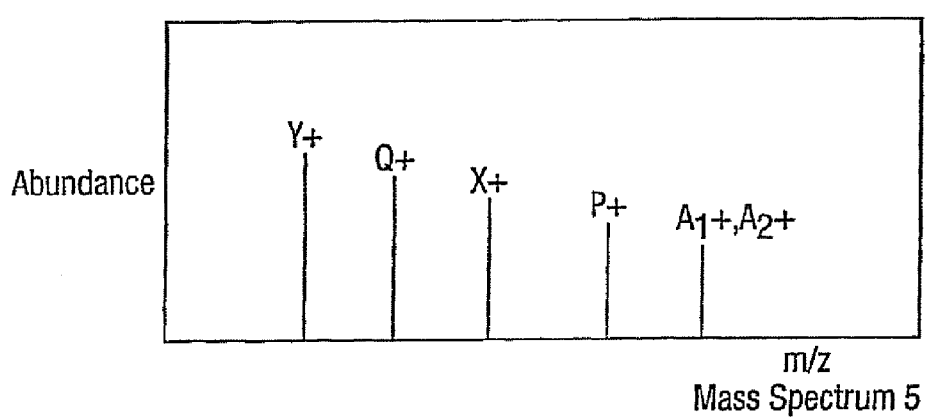
Figure 16:
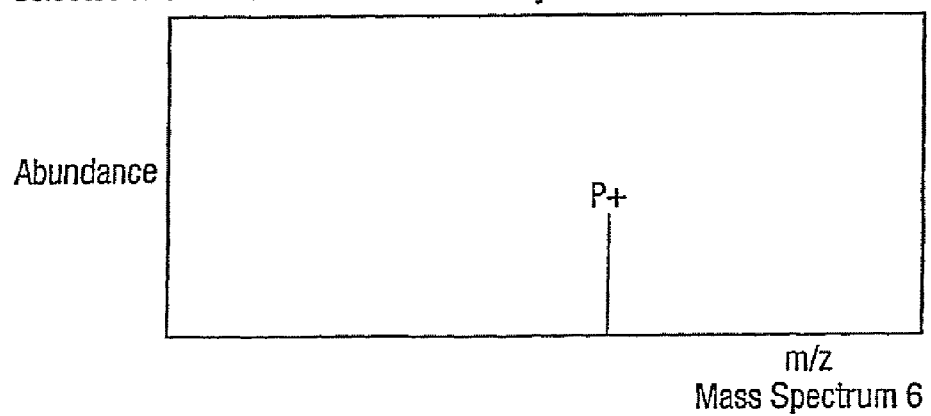
Figure 17:
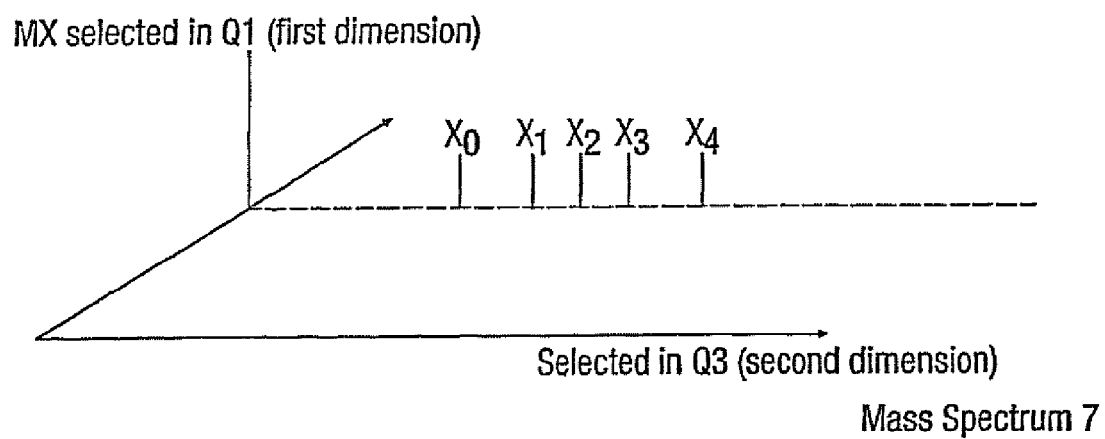
Figure 18:
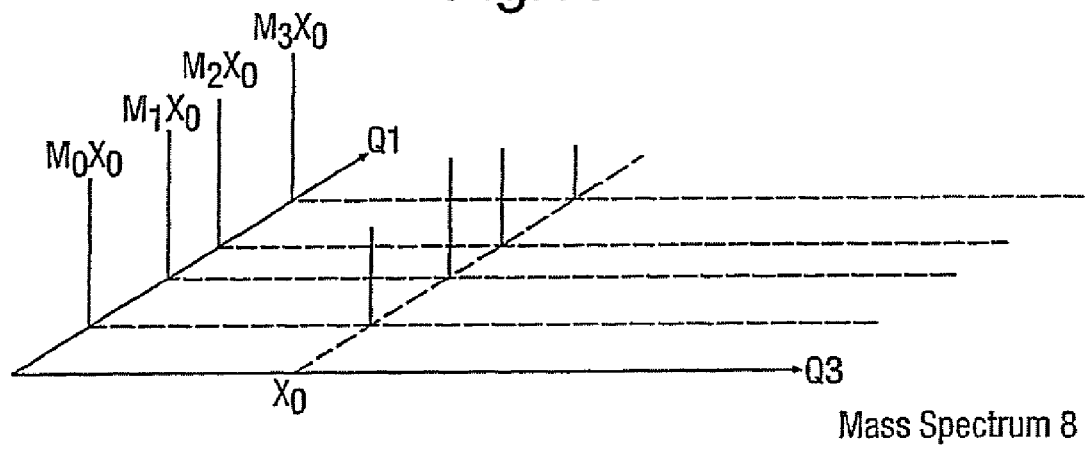
Figure 19:
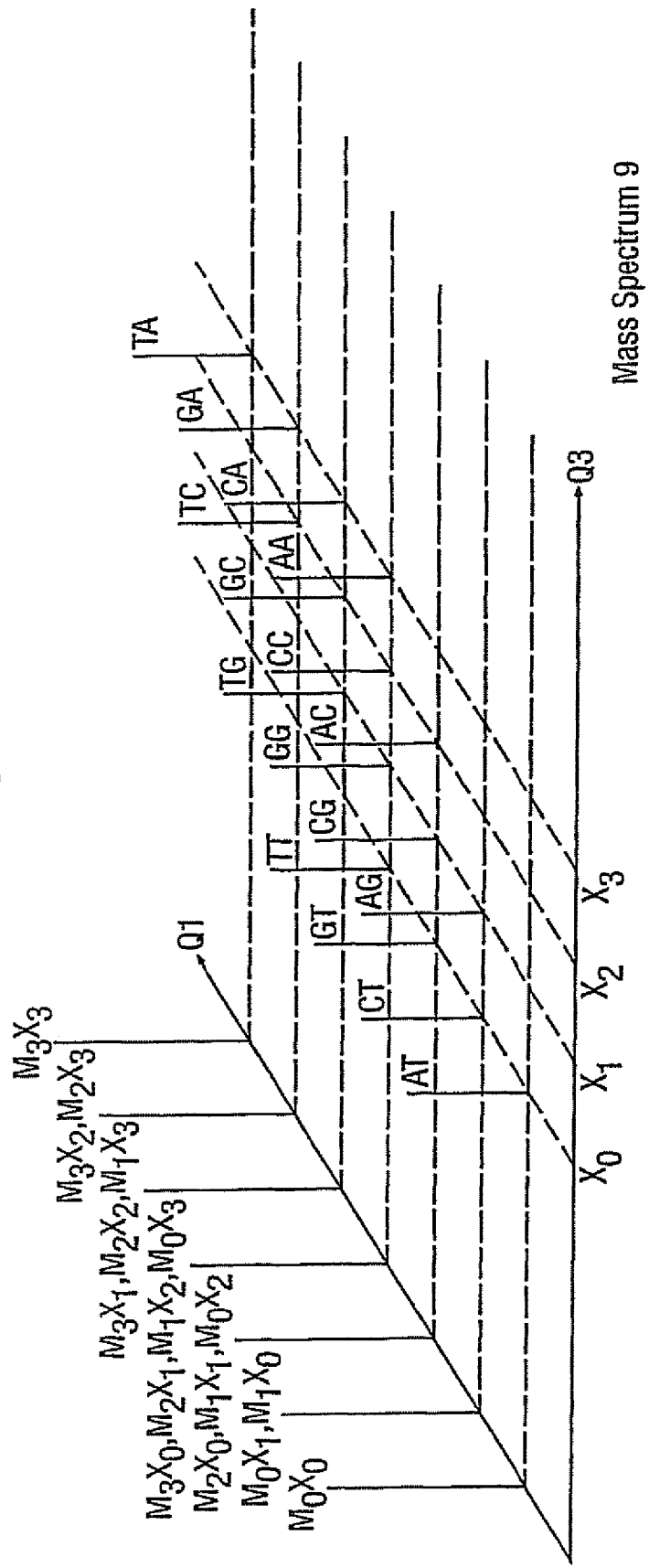
Figure 20:
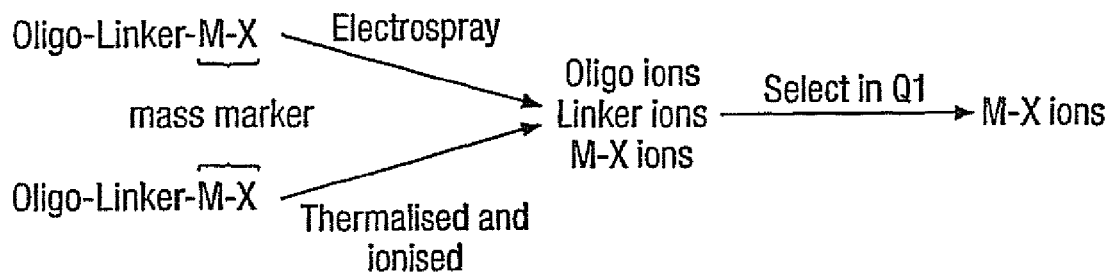
Figure 21:
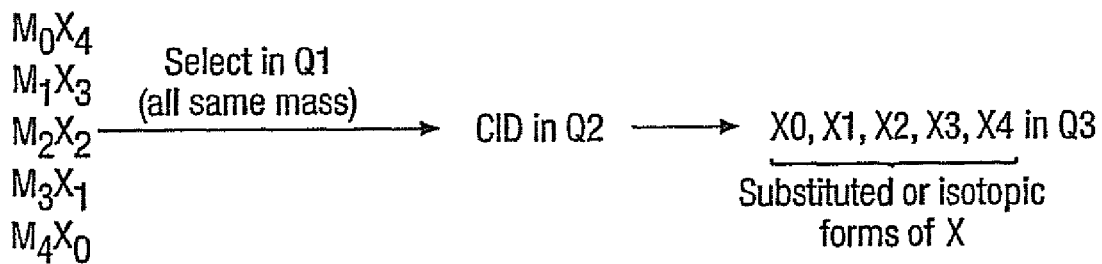

FIG. 9 illustrates the "mixing mode" embodiment of the present invention, showing 8 of the 243 possible unique mass spectra for all combinations of three mass labels P, Q, R, S and T when present in relative quantities of 0, 1 or 2 (there are 81 possible spectra if T remains constant as an internal standard);

FIG. 10 shows how larger sets of labels can be formed by enlarging the mass normalisation and mass marker moieties to allow more scope for substitution—this set of labels has nine members, and uses fluorine atom substituents as mass adjuster moieties—a set of labels having at least 8 members such as this is convenient for labelling all 256 4-mers in an array of oligonucleotides using the mixing mode of the present invention;

FIG. 11 shows mass spectrum 1, which is a complete spectrum comprising peaks from all ions $A^+$, $B^+$, $C^+$, and $D^+$;

FIG. 12 shows mass spectrum 2, which is a spectrum of $A^+$ only, produced by selecting for $A^+$ ions in a first quadrupole of the spectrometer (Q1);

FIG. 13 shows mass spectrum 3, which is a spectrum of a first ion $A_1^+$ (of the same mass/charge ratio as $A^+$) and fragmentation products of $A_1^+$, $P^+$ and $Q^+$;

FIG. 14 shows mass spectrum 4, which is a spectrum of a second ion $A_2^+$ (of the same mass/charge ratio as $A^+$) and fragmentation products of $A_2^+$, $X^+$ and $Y^+$;

FIG. 15 shows mass spectrum 5, which is a spectrum formed by selecting for A+ ions when two types of such ions are present, $A_1^+$ and $A_2^+$;

FIG. 16 shows mass spectrum 6, which is a spectrum formed in a triple quadrupole spectrometer by selecting in Q1 for A+ ions when two types of such ions are present ($A_1^+$ and $A_2^+$) inducing dissociation of the selected ions by collision in Q2, and selecting for a known collision product of $A_1^+$ (P+) in Q3—such a procedure allows resolution of $A_1^+$ and $A_2^+$;

FIG. 17 shows mass spectrum 7, which is a 2-dimensional spectrum of a set of five mass labels according to the present invention, in which a mass MX is selected in Q1 (first dimension) and five distinct masses $X_0$, $X_1$, $X_2$, $X_3$, and $X_4$ are selected in Q3 (second dimension);

FIG. 18 shows mass spectrum 8, which is a 2-dimensional spectrum of a set of four mass labels according to the present invention, in which four distinct masses, $M_0X_0$, $M_1X_0$, $M_2X_0$, and $M_3X_0$, are selected in Q1 (first dimension) and a single mass $M_0$ is selected in Q3 (second dimension);

FIG. 19 shows mass spectrum 9, which is a 2-dimensional spectrum of a set of mass labels comprising labels formed from all combinations of $M_0$-$M_3$ with $X_0$-$X_3$, in which seven distinct masses are selected in Q1 (first dimension) and four distinct masses $X_0$-$X_3$ are selected in Q3 (second dimension);

FIG. 20 shows a schematic of a typical cleavage process using the mass labels of the present invention and cleaving them from their analytes thermally, or using electrospray ionisation;

FIG. 21 shows a schematic of the selection procedures in 2-dimensional mass spectrometry using a set of five mass labels according to the present invention.

Figure 22:
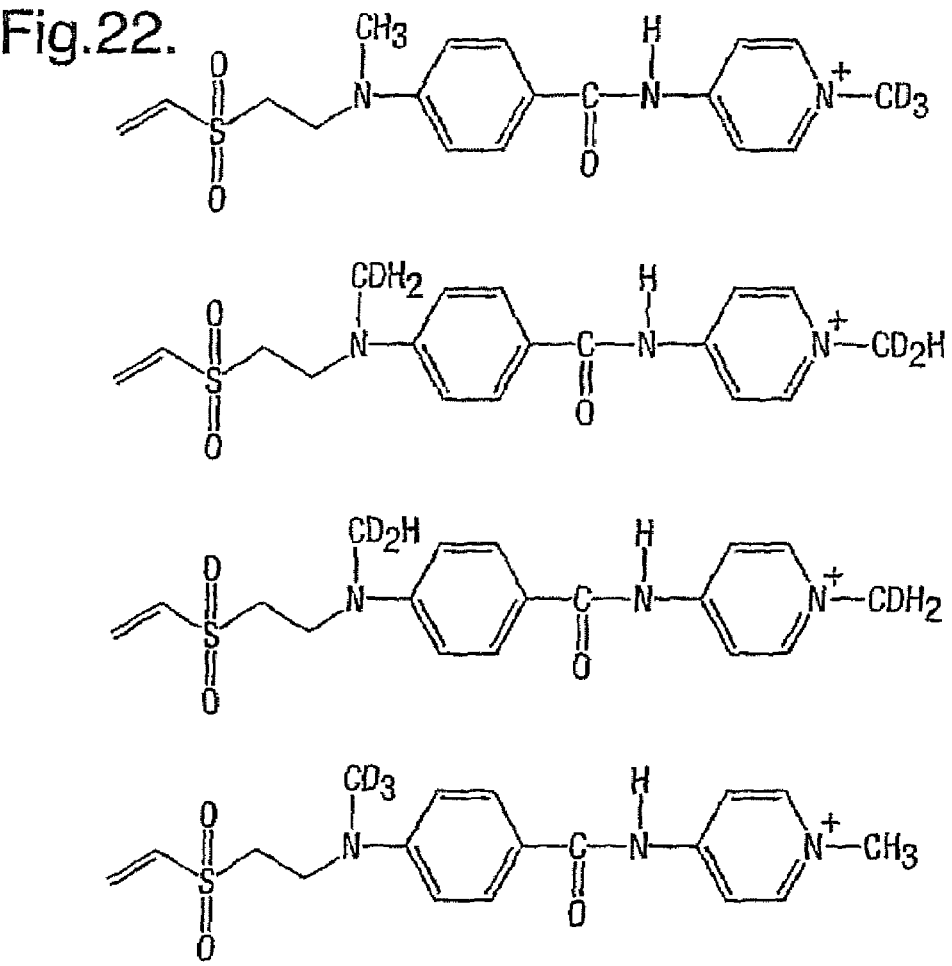
Figure 23:
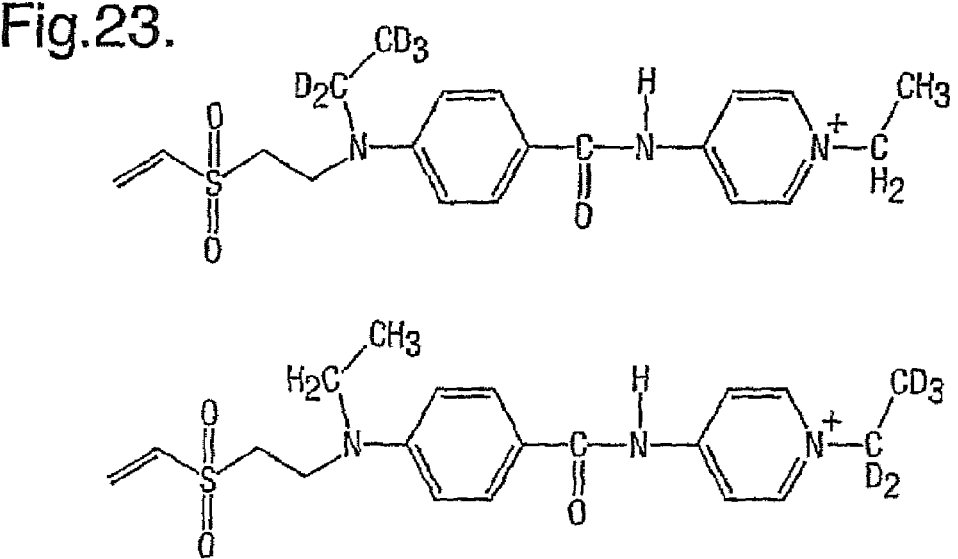
Figure 24:
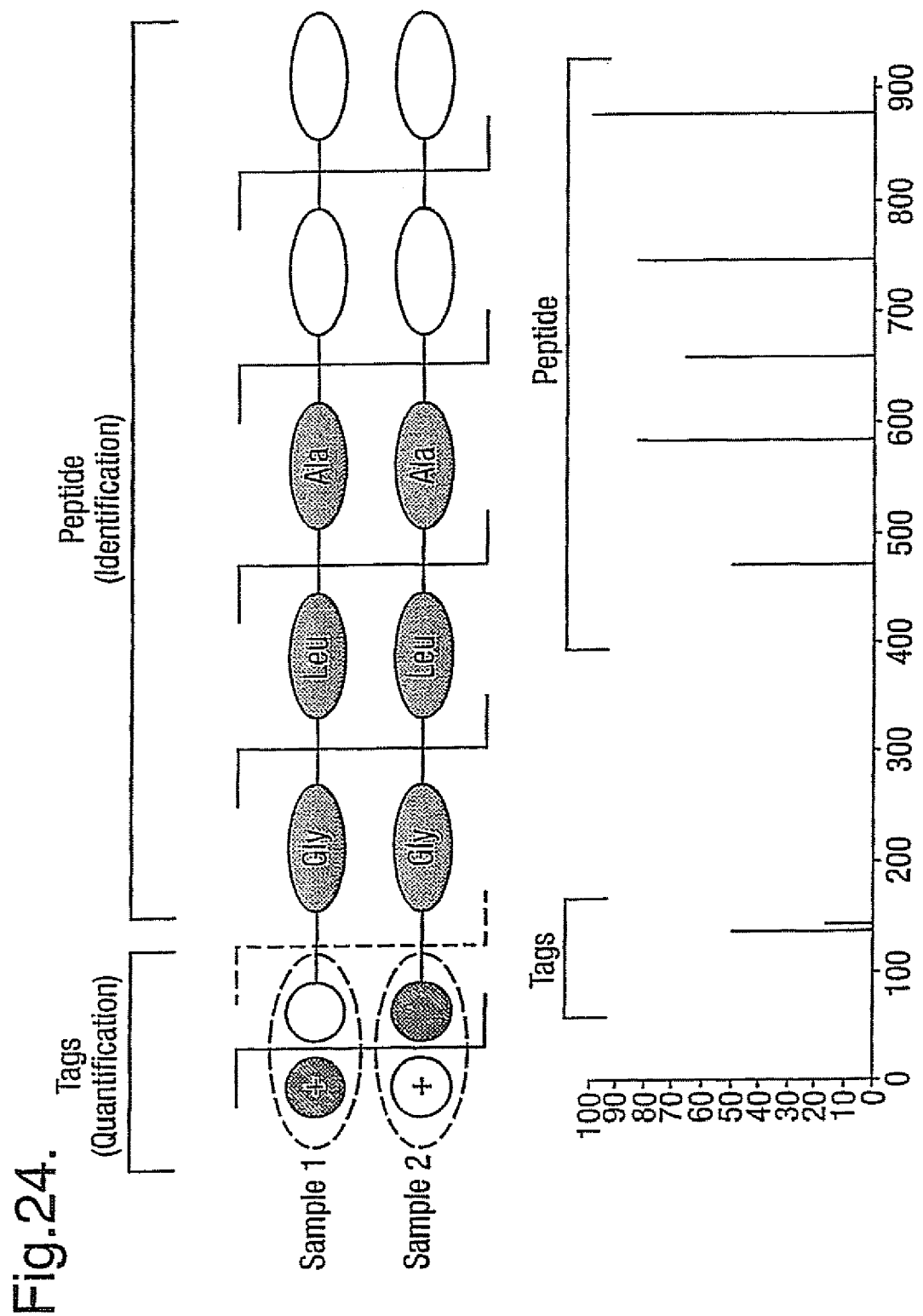

FIG. 22 shows deuterated mass labels according to the present invention;

FIG. 23 shows further deuterated mass labels according to the present invention; and FIG. 24 shows a theoretical spectrum for two samples of a peptide with the sequence H2N-gly-leu-ala-ser-glu-COOH (SEQ ID NO: 1), where each sample is attached to one of the labels with the formulae shown in FIG. 23.

In one preferred embodiment, the present invention provides a set of mass labels as defined above, in which each label in the set has a mass marker moiety having a common mass and each label in the set has a unique aggregate mass. An example a set of labels of this first type is given in FIG. 4.

In an alternative, more preferred embodiment, each label in the set has a common aggregate mass and each label in the set has a mass marker moiety of a unique mass. An example of a set of labels of this second type is given in FIG. 3.

The set of labels need not be limited to the two preferred embodiments described above, and may for example comprise labels of both types, provided that all labels are distinguishable by mass spectrometry, as outlined above.

It is preferred that, in a set of labels of the second type, each mass marker moiety in the set has a common basic structure and each mass normalisation moiety in the set has a common basic structure, and each mass label in the set comprises one or more mass adjuster moieties, the mass adjuster moieties being attached to or situated within the basic structure of the mass marker moiety and/or the basic structure of the mass normalisation moiety. In this embodiment, every mass marker moiety in the set comprises a different number of mass adjuster moieties and every mass label in the set has the same number of mass adjuster moieties.

Throughout this description, by common basic structure, it is meant that two or more moieties share a structure which has substantially the same structural skeleton, backbone or core. This skeleton or backbone may be for example a phenyl ether moiety. The skeleton or backbone may comprise substituents pendent from it, or atomic or isotopic replacements within it, without changing the common basic structure.

Typically, a set of mass labels of the second type referred to above comprises mass labels with the formula:

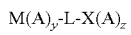

wherein M is the mass normalisation moiety, X is the mass marker moiety, A is a mass adjuster moiety, L is a cleavable linker, y and z are integers of 0 or greater, and y+z is an integer of 1 or greater. Preferably M is a fragmentation resistant group, L is a linker that is susceptible to fragmentation on collision with another molecule or atom and X is preferably a pre-ionised, fragmentation resistant group. The sum of the masses of M and X is the same for all members of the set. Preferably M and X have the same basic structure or core structure, this structure being modified by the mass adjuster moieties. The mass adjuster moiety ensures that the sum of the masses of M and X in is the same for all mass labels in a set, but ensures that each X has a distinct (unique) mass.

A preferred set of mass labels having the above structure is one wherein each of the labels in the set has the following structure:

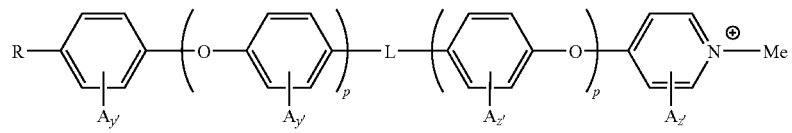

wherein R is hydrogen or is a substituted or unsubstituted aliphatic, aromatic, cyclic or heterocyclic group, L is the cleavable linker and A is the mass adjuster moiety, each p is the same and is an integer of 0 or greater, each y' may be the same or different and is an integer of 0-4, the sum of all y' being equal to y, each z' may be the same or different and is an integer of 0-4, the sum of all z' being equal to z. Preferably R is H, L is an amide bond, p=0, and A is an F atom.

In the present context, the substitution pattern on the R group is not at all limited. The substituent or substituents may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group may comprise a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but generally the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but the ring of the cyclic group may comprise from 3-10 atoms, such as 3, 4, 5, 6 or 7 atoms.

The groups comprising heteroatoms defined above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups. The substituent may also comprise derivatives of these groups, such as carboxylic acid anhydrides and carboxylic acid halides.

In addition, any substituent may comprise a combination of two or more of the substituents and/or functional groups defined above.

The arrays of mass labels of the present invention are not particularly limited, provided that they contain a plurality of sets of mass labels according to the present invention. It is preferred that the arrays comprise two or more, three or more, four or more, or five or more sets of mass labels. Preferably each mass label in the array has either of the following structures:

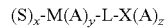

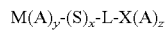

wherein S is the mass series modifying group, M is the mass normalisation moiety, X is the mass marker moiety, A is the mass adjuster moiety, L is the cleavable linker, x is an integer of 0 or greater, y and z are integers of 0 or greater, and y+z is an integer of 1 or greater.

Figure 7:
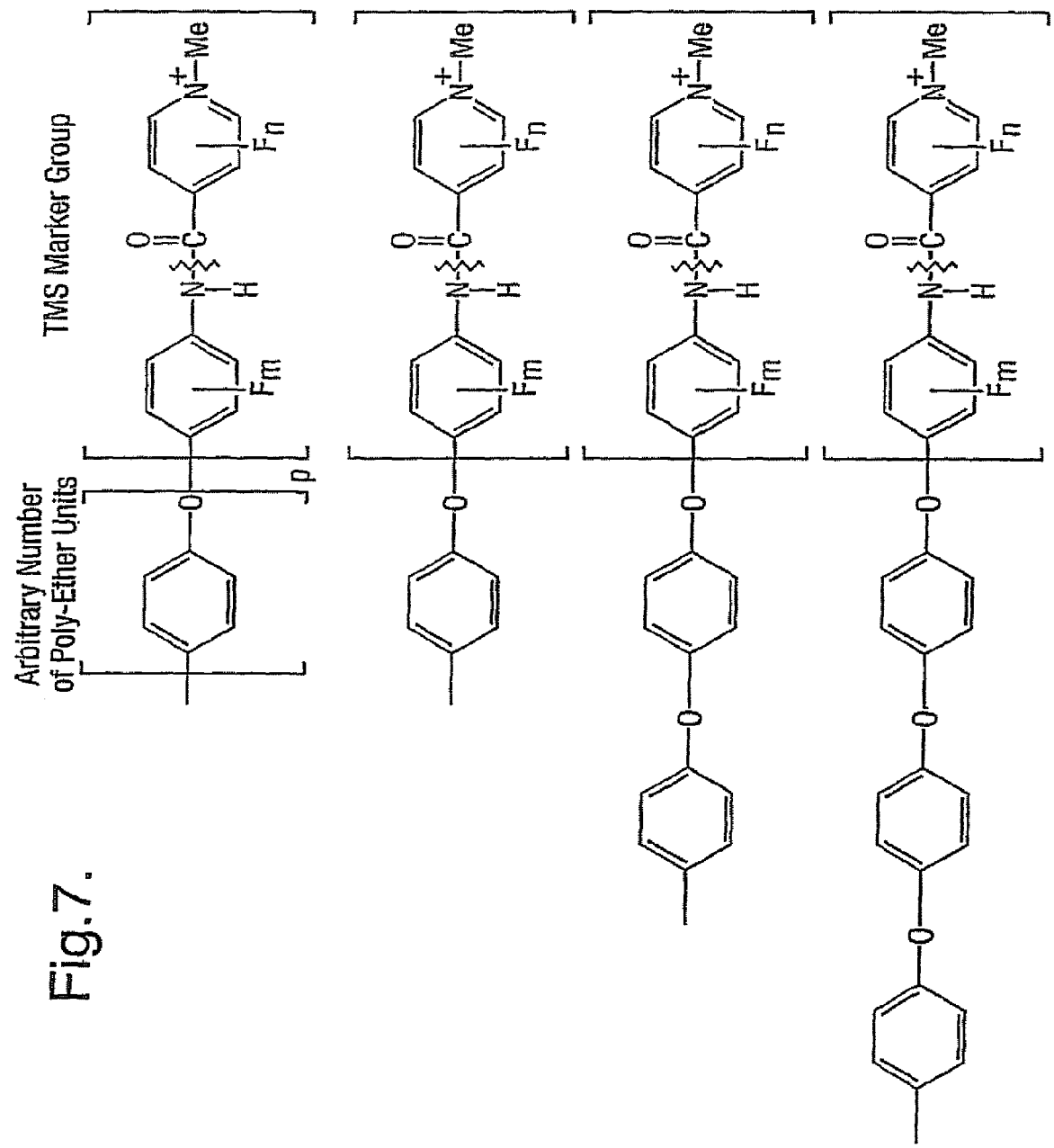
FIG. 7 shows an array of sets of mass labels, each set having the same mass series modifying group (S) and being distinct from all other sets by virtue of the number of phenyl ether units in the mass series modifying group.

A preferred array of mass labels of the above type is one in which the mass labels have either of the following structures:

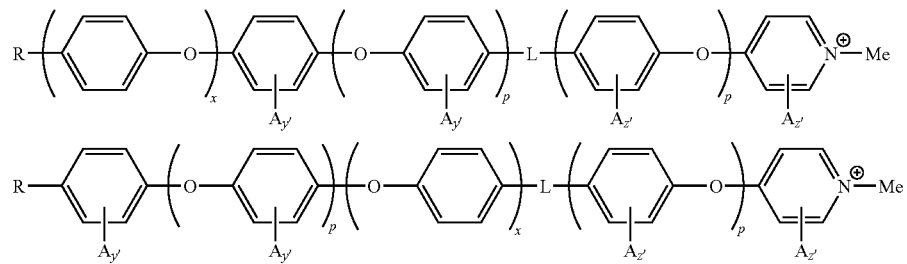

wherein R is hydrogen or is a substituted or unsubstituted aliphatic, aromatic, cyclic or heterocyclic group, each p is the same and is an integer of 0 or greater, x is an integer of 0 or greater each x for any one set being different from the x of every other set in the array, each y' may be the same or different and is an integer of 0-4, the sum of all y' being equal to y, and each z' may be the same or different and is an integer of 0-4, the sum of all z' being equal to z. An array of this type is depicted in FIG. 7.

In an alternative preferred aspect, the array of mass labels may comprise mass labels having either of the following structures:

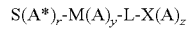

wherein S is a mass series modifying group, M is the mass normalisation moiety, X is the mass marker moiety, A is a mass adjuster moiety of the mass marker and mass normalisation moieties, A* may be the same or different from A and is a mass adjuster moiety of the mass series modifying groups, L is the cleavable linker, r is an integer of 0 or greater and is at least 1 for one or more sets of mass labels in the array, y and z are integers of 0 or greater, and x+y is an integer of 1 or greater. Preferably, M is a fragmentation resistant group, L is a linker that is susceptible to fragmentation on collision with another molecule or atom and X is preferably a pre-ionised, fragmentation resistant group. S is typically a group such that each member of the array of sets of labels comprises an S whose mass is separated by preferably 4 daltons from every other S of every other member of the array. Thus each different set of mass labels has a distinct (unique) mass.

Figure 6:
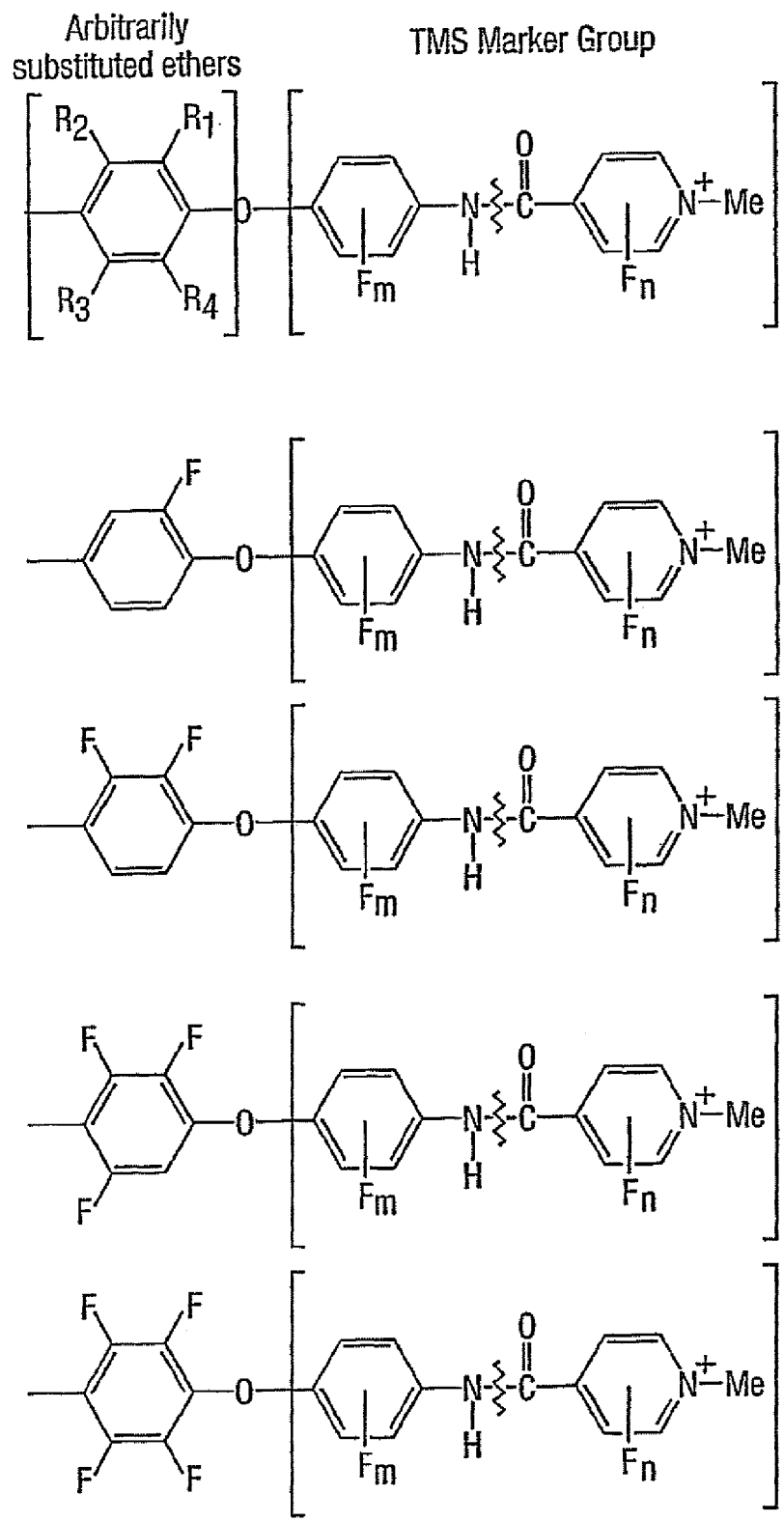
FIG. 6 shows an array of sets of mass labels, each set having the same mass series modifying group (S) and being distinct from all other sets by virtue of the number of fluorine substituents on the base phenyl group.

A preferred array of mass labels of the above latter type is one in which the mass labels in the array has either of the following structures:

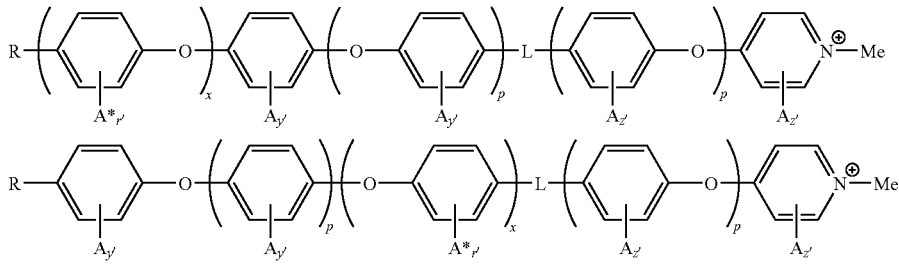

wherein R is hydrogen or is a substituted or unsubstituted aliphatic, aromatic, cyclic or heterocyclic group, each p is the same and is an integer of 0 or greater, x is an integer of 0 or greater x being the same for all mass labels in the array, each y' may be the same or different and is an integer of 0-4, the sum of all y' being equal to y, each z' may be the same or different and is an integer of 0-4, the sum of all z' being equal to z, and each r' may be the same or different, the sum of all r' being equal to r. An array of this type is depicted in FIG. 6.

In the above sets and arrays of this invention, the common basic structure of the M, X and S groups is not particularly limited and may comprise a cyclic and/or a non-cyclic group. The nature of M, X and S is not particularly limited. However, it is preferred that M and/or X, and/or S comprise as a basic (core) structure, a cyclic group, such as an aryl, a cycloalkyl or a heterocyclic group. These groups may be unsubstituted, but are preferably substituted. M, X and/or S may respectively comprise an oligomer or polymer formed from the above cyclic monomers, where the cyclic monomers are linked by a fragmentation resistant bond or group.

Aryl ethers, such as a phenyl ether group and their oligomers and polymers, especially substituted aryl ethers, are preferred common basic structures for M, X and S.

The cleavable linker group L is not particularly limited. However, it is preferred that L comprises a group which is cleavable by collision, and/or is cleavable in a mass spectrometer. Preferably the group L comprises an amide bond.

In a further preferred aspect, this invention provides sets and arrays of mass labels which can be reacted with analyte molecules, the mass labels having the form:

Re-L'-label or Re-L'-S-label where Re is a reactive functionality or group which allows the mass label to be reacted covalently to an appropriate functional group in an analyte molecule, such as, but not limited to, a nucleotide oligonucleotide, polynucleotide, amino acid, peptide or polypeptide. L' is a linker which may or may not be cleavable, and label is a mass label from any of the sets or arrays defined above. S has the same meaning as defined above. L' may be a cleavable linker if desired, such as a cleavable linker L, as defined above.

In preferred embodiments of the above aspects of the invention, L and/or L' are cleavable within the mass spectrometer and preferably within the ion source of the mass spectrometer.

Linker Groups

In the discussion above and below reference is made to linker groups which may be used to connect molecules of interest to the mass label compounds of this invention. A variety of linkers is known in the art which may be introduced between the mass labels of this invention and their covalently attached analyte. Some of these linkers may be cleavable. Oligo- or poly-ethylene glycols or their derivatives may be used as linkers, such as those disclosed in Maskos, U. & Southern, E. M. Nucleic Acids Research 20: 1679-1684, 1992. Succinic acid based linkers are also widely used, although these are less preferred for applications involving the labelling of oligonucleotides as they are generally base labile and are thus incompatible with the base mediated deprotection steps used in a number of oligonucleotide synthesizers.

Propargylic alcohol is a bifunctional linker that provides a linkage that is stable under the conditions of oligonucleotide synthesis and is a preferred linker for use with this invention in relation to oligonucleotide applications. Similarly 6-aminohexanol is a useful bifunctional reagent to link appropriately funtionalised molecules and is also a preferred linker.

A variety of known cleavable linker groups may be used in conjunction with the compounds of this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labelling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labelling of oligonucleotides. The content of this application is incorporated by reference.

In the discussion below, reference is made to reactive functionalities, Re, to allow compounds of the invention to be linked to other compounds, whether reporter groups or analyte molecules. A variety of reactive functionalities may be introduced into the mass labels of this invention.

Table 1 below lists some reactive functionalities that may be reacted with nucleophilic functionalities which are found in biomolecules to generate a covalent linkage between the two entities. For applications involving synthetic oligonucleotides, primary amines or thiols are often introduced at the termini of the molecules to permit labelling. Any of the functionalities listed below could be introduced into the compounds of this invention to permit the mass markers to be attached to a molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —SO$_2$—CH═CR$_2$ | —S—CR$_2$—CH$_2$—SO$_2$— |
| —NH$_2$ | —SO$_2$—CH═CR$_2$ | —N(CR$_2$—CH$_2$—SO$_2$—)$_2$ or —NH—CR$_2$—CH$_2$—SO$_2$— |
| —NH$_2$ | N-hydroxysuccinimide ester | —CO—NH— |
| —NH$_2$ | N-hydroxybenzotriazole ester | —CO—NH— |
| —NH$_2$ | —NCO | —NH—CO—NH— |
| —NH$_2$ | —NCS | —NH—CS—NH— |
| —NH$_2$ | —CHO | —CH$_2$—NH— |
| —NH$_2$ | —SO$_2$Cl | —SO$_2$—NH— |
| —NH$_2$ | —CH═CH— | —NH—CH$_2$—CH$_2$— |
| —OH | —OP(NCH(CH$_3$)$_2$)$_2$ | —OP(═O)(O)O— |

It should be noted that in applications involving labelling oligonucleotides with the mass markers of this invention, some of the reactive functionalities above or their resultant linking groups might have to be protected prior to introduction into an oligonucleotide synthesiser. Preferably unprotected ester, thioether and thioesters, amine and amide bonds are to be avoided, as these are not usually stable in an oligonucleotide synthesiser. A wide variety of protective groups is known in the art which can be used to protect linkages from unwanted side reactions.

In the discussion below reference is made to "charge carrying functionalities" and solubilising groups. These groups may be introduced into the mass labels such as in the mass markers of the invention to promote ionisation and solubility. The choice of markers is dependent on whether positive or negative ion detection is to be used. Table 2 below lists some functionalities that may be introduced into mass markers to promote either positive or negative ionisation. The table is not intended as an exhaustive list, and the present invention is not limited to the use of only the listed functionalities.

TABLE 2

| Positive Ion Mode | Negative Ion Mode |
|---|---|
| —NH$_2$ | —SO$_3^-$ |
| —NR$_2$ | —PO$_4^-$ |
| —NR$_3^+$ | —PO$_3^-$ |
| guanidinium group | —CO$_2^-$ |
| N-alkylpyridinium group | |
| —SR$_2^+$ | |

WO 00/02893 discloses the use of metal-ion binding moieties such as crown-ethers or porphyrins for the purpose of improving the ionisation of mass markers. These moieties are also be applicable for use with the mass markers of this invention.

The components of the mass markers of this invention are preferably fragmentation resistant so that the site of fragmentation of the markers can be controlled by the introduction of a linkage that is easily broken by Collision Induced Dissociation. Aryl ethers are an example of a class of fragmentation resistant compounds that may be used in this invention. These compounds are also chemically inert and thermally stable. WO 99/32501 discusses the use of poly-ethers in mass spectrometry in greater detail and the content of this application is incorporated by reference.

In the past, the general method for the synthesis of aryl ethers was based on the Ullmann coupling of arylbromides with phenols in the presence of copper powder at about 200° C. (representative reference: H. Stetter, G. Duve, Chemische Berichte 87 (1954) 1699). Milder methods for the synthesis of aryl ethers have been developed using a different metal catalyst but the reaction temperature is still between 100 and 120° C. (M. Iyoda, M. Sakaitani, H. Otsuka, M. Oda, Tetrahedron Letters 26 (1985) 477). This is a preferred route for the production of poly-ether mass labels. See synthesis of FT77 given in the examples below. A recently published method provides a most preferred route for the generation of poly-ether mass labels as it is carried out under much milder conditions than the earlier methods (D. E. Evans, J. L. Katz, T. R. West, Tetrahedron Lett. 39 (1998) 2937).

The present invention also provides a set of two or more probes, each probe in the set being different and being attached to a unique mass label or a unique combination of mass labels, from a set or an array of mass labels as defined as defined above.

Further provided is an array of probes comprising two or more sets of probes, wherein each probe in any one set is attached to a unique mass label, or a unique combination of mass labels, from a set of mass labels as defined above, and wherein the probes in any one set are attached to mass labels from the same set of mass labels, and each set of probes is attached to mass labels from unique sets of mass labels from an array of mass labels as defined above.

In one embodiment, each probe is preferably attached to a unique combination of mass labels, each combination being distinguished by the presence or absence of each mass label in the set of mass labels and/or the quantity of each mass label attached to the probe. This is termed the "mixing mode" of the present invention, since the probes may be attached to a mixture of mass labels.

In the above aspects, the nature of the probe is not particularly limited. However, preferably each probe comprises a biomolecule. Any biomolecule can be employed, but the biomolecule is preferably selected from a DNA, an RNA, an oligonucleotide, a nucleic acid base, a peptide, a polypeptide, a protein and an amino acid.

In one preferred embodiment, this invention provides sets and arrays of mass labelled analytes, such as nucleotides, oligonucleotides and polynucleotides, of the form:

Analyte-L'-label or Analyte-L'-S-label

Wherein L' and S are as defined above, and label is a mass label from any of the sets and arrays defined above.

In the above aspect, the nature of the analyte is not particularly limited. However, preferably each analyte comprises a biomolecule. Any biomolecule can be employed, but the biomolecule is preferably selected from a DNA, an RNA, an oligonucleotide, a nucleic acid base, a peptide, a polypeptide, a protein and an amino acid.

In one embodiment, each analyte is preferably attached to a unique combination of mass labels, each combination being distinguished by the presence or absence of each mass label in the set of mass labels and/or the quantity of each mass label attached to the probe. As mentioned above, this is termed the "mixing mode" of the present invention, since the probes may be attached to a mixture of mass labels.

As mentioned above, the present invention provides a method of analysis, which method comprises detecting an analyte by identifying by mass spectrometry a mass label or a combination of mass labels unique to the analyte, wherein the mass label is a mass label from a set or an array of mass labels as defined above. The type of method is not particularly limited, provided that the method benefits from the use of the mass labels of the present invention to identify an analyte. The method may be, for example, a method of sequencing nucleic acid or a method of profiling the expression of one or more genes by detecting quantities of protein in a sample. The method is especially advantageous, since it can be used to readily analyse a plurality of analytes simultaneously. However, the method also has advantages for analysing single analytes individually, since using the present mass labels, mass spectra which are cleaner than conventional spectra are produced, making the method accurate and sensitive.

In a further preferred embodiment, the present invention provides a method which method comprises:
    (a) contacting one or more analytes with a set of probes, or an array of probes, each probe in the set or array being specific to at least one analyte, wherein the probes are as defined above,
    (b) identifying an analyte, by detecting the probe specific to that analyte.

In this embodiment it is preferred that the mass label is cleaved from the probe prior to detecting the mass label by mass spectrometry.

The nature of the methods of this particular embodiment is not especially limited. However, it is preferred that the method comprises contacting one or more nucleic acids with a set of hybridisation probes. The set of hybridisation probes typically comprises a set of up to 256 4-mers, each probe in the set having a different combination of nucleic acid bases. This method may be suitable for identifying the presence of target nucleic acids, or alternatively can be used in a stepwise method of primer extension sequencing of one or more nucleic acid templates.

The mass labels of the present invention are particularly suitable for use in methods of 2-dimensional analysis, primarily due to the large number of labels that can be simultaneously distinguished. The labels may thus be used in a method of 2-dimensional gel electrophoresis, or in a method of 2-dimensional mass spectrometry.

Thus, in one aspect the present invention provides a method of 2-dimensional mass spectrometric analysis, which method comprises:
    (a) providing one or more analytes, each analyte being labelled with a mass label or a combination of mass labels unique to that analyte, wherein the mass labels are from a set or array of mass labels as defined above;
    (b) cleaving the mass labels from the analytes;
    (c) detecting the mass labels;
    (d) dissociating the mass labels in the mass spectrometer, to release the mass marker moieties from the mass normalisation moieties;
    (e) detecting the mass marker moieties; and
    (f) identifying the analytes on the basis of the mass spectrum of the mass labels in the first dimension and the mass spectrum of the mass marker moieties in the second dimension.

In this method, preferably in step (c) mass labels of a chosen mass or a chosen range of masses are selected for detection. It is also preferred that in step (e) mass marker moieties having a specific mass or a specific range of masses are selected for detection.

In another aspect, the present invention provides a method of analysis, which method comprises:
    (a) subjecting a mixture of labelled analytes to a first separation treatment on the basis of a first property of the analytes;
    (b) subjecting the resulting separated analytes to a second separation treatment on the basis of a second property of the analytes; and
    (c) detecting an analyte by detecting its label;

wherein the analytes are labelled with a mass label from a set or an array of mass labels as defined above.

The property of the analytes is not particularly limited. However, in this embodiment in step (a) and/or step (b) the analytes are preferably separated according to their length or mass. It is further preferred that in step (a) and/or step (b) the analytes are separated according to their iso-electric point. Typically, the analytes comprise one or more proteins, polypeptides, peptides, amino acids or nucleic acids, or fragments thereof. It is particularly preferred that gel electrophoresis is employed in each of the separation steps. In this embodiment, the method is a method of 2-dimensional gel electrophoresis.

In a further aspect, the present invention provides a method for characterising nucleic acid, which comprises:
    (a) providing a population of nucleic acid fragments, each fragment having cleavably attached thereto a mass label from a set or an array of mass labels as defined above for identifying a feature of that fragment;
    (b) separating the fragments on the basis of their length;
    (c) cleaving each fragment to release its mass label; and
    (d) determining each mass label by mass spectroscopy to relate the feature of each fragment to the length of the fragment.

Typically, the method of this aspect of the invention is used for characterising cDNA. Preferably, this method comprises:

(a) exposing a sample comprising a population of one or more cDNAs or fragments thereof to a cleavage agent which recognises a predetermined sequence and cuts at a reference site at a known displacement from the predetermined sequence proximal to an end of each cDNA or fragment thereof so as to generate a population of terminal fragments;
(b) ligating to each reference site an adaptor oligonucleotide which comprises a recognition site for a sampling cleavage agent;
(c) exposing the population of terminal fragments to a sampling cleavage agent which binds to the recognition site and cuts at a sampling site of known displacement from the recognition site so as to generate in each terminal fragment a sticky end sequence of a predetermined length of up to 6 bases, and of unknown sequence;
(d) separating the population of terminal fragments into sub-populations according to sequence length; and
(e) determining each sticky end sequence by:
   (i) probing with an array of labelled hybridisation probes, the array containing all possible base sequences of the predetermined length;
   (ii) ligating those probes which hybridised to the sticky end sequences; and
   (iii) determining which probes are ligated by identification and preferably quantification of the labels;

wherein the labels are mass labels from a set or an array as defined above.

In this method, the population of terminal fragments is preferably separated by capillary electrophoresis, HPLC or gel electrophoresis.

In a still further aspect of the present invention, there is provided a method for characterising nucleic acid, which method comprises generating Sanger ladder nucleic acid fragments from one or more nucleic acid templates, in the presence of at least one labelled terminating base, and identifying the length of the fragment, and the terminating base of the fragment, wherein the label is specific to the terminating base and is a mass label from a set or an array as defined above.

In this aspect of the invention, it is preferred that all four terminating bases are present in the same reaction zone. The method typically comprises generating Sanger ladder nucleic acid fragments from a plurality of nucleic acid templates present in the same reaction zone, and for each nucleic acid fragment produced identifying the length of the fragment, the identity of the template from which the fragment is derived and the terminating base of the fragment, wherein prior to generating the fragments, a labelled primer nucleotide or oligonucleotide is hybridised to each template, the label on each primer being specific to the template to which that primer hybridises to allow identification of the template. The type of label identifying the template is not particularly limited. However, it is preferred that the label identifying the template is a mass label from a set or an array as defined in above.

A further aspect of the method of the present invention provides a method for sequencing nucleic acid, which method comprises:
(a) obtaining a target nucleic acid population comprising one or more single-stranded DNAs to be sequenced, each of which is present in a unique amount and bears a primer to provide a double-stranded portion of the nucleic acid for ligation thereto;
(b) contacting the nucleic acid population with an array of hybridisation probes, each probe comprising a label cleavably attached to a known base sequence of predetermined length, the array containing all possible base sequences of that predetermined length and the base sequences being incapable of ligation to each other, wherein the contacting is carried out in the presence of ligase under conditions to ligate to the double-stranded portion of each nucleic acid the probe bearing the base sequence complementary to the single-stranded nucleic acid adjacent the double-stranded portion thereby to form an extended double-stranded portion which is incapable of ligation to further probes; and
(c) removing all unligated probes; followed by the steps of:
(d) cleaving the ligated probes to release each label;
(e) recording the quantity of each label; and
(f) activating the extended double-stranded portion to enable ligation thereto; wherein
(g) steps (b) to (f) are repeated in a cycle for a sufficient number of times to determine the sequence of the or each single-stranded nucleic acid by determining the sequence of release of each label, wherein the labels of the hybridisation probes are each from a set or an array as defined above.

In this aspect of the invention, it is preferred that the hybridisation probes are a set of 256 4-mers, each probe in the set having a different combination of nucleic acid bases.

As already mentioned, it is preferred in all of the above aspects of the present methods that two or more analytes are detected by simultaneously identifying their mass labels or combinations of mass labels by mass spectrometry.

The mixing mode of the present invention may be applied to all of the above methods. In this embodiment, each analyte is identified by a unique combination of mass labels from a set or array of mass labels, each combination being distinguished by the presence and absence of each mass label in the set or array and/or the quantity of each mass label.

If the method is applied to two or more analytes simultaneously, in some aspects it is preferred that the analytes are separated according to their mass, prior to detecting the mass label by mass spectrometry. Preferably, the separation step is a chromatographic step, such as liquid chromatography or gel electrophoresis. The present labels of type 2 are particularly advantageous in these embodiments, since the aggregate mass of all labels in the set is the same, thus during a chromatographic separation step, the mobility of all analytes is equally affected by the labels.

Typically, in the present methods, the mass spectrometer employed to detect the mass label comprises one or more mass analysers, which mass analysers are capable of allowing ions of a particular mass, or range of masses, to pass through for detection and/or are capable of causing ions to dissociate. Preferably ions of a particular mass or range of masses specific to one or more known mass labels are selected using the mass analyser, the selected ions are dissociated, and the dissociation products are detected to identify ion patterns indicative of the selected mass labels. In particularly preferred methods, the mass spectrometer comprises three quadrupole mass analysers. In this embodiment, generally a first mass analyser is used to select ions of a particular mass or mass range, a second mass analyser is used to dissociate the selected ions, and a third mass analyser is used to detect resulting ions.

A preferred embodiment of the above methods provides a method of analysing mass labelled analyte molecules, comprising the steps of:
1. Cleaving the mass label from its associated molecule of interest.
2. Ionising the cleaved mass label.
3. Selecting ions of a predetermined mass to charge ratio corresponding to the mass to charge ratio of the preferred ions of known mass labels in a mass analyser.
4. Inducing dissociation of these selected ions by collision.

5. Detecting the collision products to identify collision product ions that are indicative of the selected mass labels.

It is preferred that the process of cleaving the mass label from its associated nucleic acid takes place within a mass spectrometer, preferably within the ion source. It is also preferred that the mass labels are pre-ionised. In this embodiment the labels need only be transferred from a liquid or solid phase into the gas phase (if the mass labels are in a liquid or solid phase). Typically, the step of ionising the mass label results from cleavage of the mass label within the ion source of the mass spectrometer.

Preferably, the third step of selecting the ions of a predetermined mass to charge ratio is performed in the first mass analyser of a serial instrument. The selected ions are then channelled into a separate collision cell where they are collided with a gas or a solid surface according to the above fourth step. The collision products are then channelled into a further mass analyser of a serial instrument to detect collision products according to the above fifth step. Typical serial instruments for use in the present invention include triple quadrupole mass spectrometers, tandem sector instruments and quadrupole time of flight mass spectrometers.

It is further preferred that the above third step of selecting the ions of a predetermined mass to charge ratio, the fourth step of colliding the selected ions with a gas and the fifth step of detecting the collision products are performed in the same zone of the mass spectrometer. This may, for example, be effected in ion trap mass analysers and Fourier Transform Ion Cyclotron Resonance mass spectrometers.

In a further preferred embodiment, the invention provides a method of analysing mass labelled analyte molecules, comprising the steps of:

1. Cleaving the mass label from its associated analyte molecule.
2. Ionising the cleaved mass label.
3. Selecting ions of a predetermined mass to charge ratio corresponding to the mass to charge ratio of the preferred ions of known mass labels in a mass analyser.
4. Inducing dissociation of these selected ions by collision.
5. Detecting more than one of the collision products to identify collision product ion patterns that are indicative of the selected mass labels which in turn identify the labelled nucleic acid.

In preferred aspects of this embodiment of this invention, the process of cleaving the mass label from its associated nucleic acid takes place within a mass spectrometer, preferably within the ion source.

In certain preferred aspects of this embodiment, the mass labels are pre-ionised and need only be transferred from a liquid or solid phase into the gas phase (if the mass labels are in a liquid or solid phase).

In other preferred aspects, the step of ionising the mass label results from cleavage of the mass label within the ion source of the mass spectrometer.

In certain aspects, the third step of selecting the ions of a predetermined mass to charge ratio is performed in the first mass analyser of a serial instrument. The selected ions are then channelled into a separate collision cell where they are collided with a gas or a solid surface according to the above fourth step. The collision products are then channelled into a further mass analyser of a serial instrument to detect collision products according to the above fifth step. Typical serial instruments include triple quadrupole mass spectrometers, tandem sector instruments and quadrupole time of flight mass spectrometers.

In other preferred aspects, the third step of selecting the ions of a predetermined mass to charge ratio, the fourth step of colliding the selected ions with a gas and the fifth step of detecting the collision products are performed in the same zone of the mass spectrometer.

This may effected in ion trap mass analysers and Fourier Transform Ion Cyclotron Resonance mass spectrometers, for example.

Tandem Mass Spectrometry

At the expense of some loss in sensitivity, great gains in selectivity can be gained through use of tandem mass spectrometry (MS/MS) to detect the mass labels of the present invention. For the purposes of illustrating the invention some discussion is now provided regarding tandem mass spectrometry, exemplified here by reference to the triple quadrupole mass spectrometer. The triple quad allows easy illustration of the principle of MS/MS.

The quadrupole mass analyser is essentially a mass filter which can at any moment be set to allow ions of only a particular mass to charge ratio to pass through. A quadrupole comprises 4 parallel rod shaped electrodes which form a channel. A direct current potential superimposed by a sinusoidal radio frequency potential is applied to the rod electrodes. Ions entering into the channel formed by the parallel rods follow complex trajectories and for a particular DC potential and radio frequency potential, only ions with a predetermined mass to charge ratio will have a stable trajectory which will lead them through the channel. By changing the applied potentials the quadrupole can be made to scan across a full range of mass to charge ratios up to about 4000.

Figure 1:
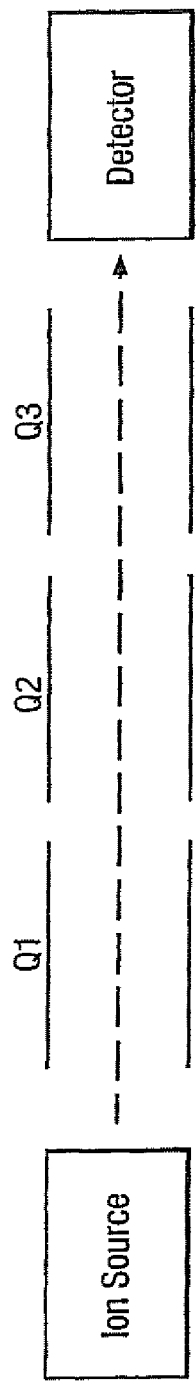
FIG. 1 shows a schematic layout of a triple quadrupole mass spectrometer.

A triple quad (Q) layout is shown in FIG. 1. Three separate quadrupole mass analysers are linked in series. The first quadrupole is referred to hereafter as Q1, similarly the second will be referred to as Q2 and the third as Q3. Quadrupoles Q1 and Q3 are typically used in scanning modes. The speed of scanning is very high. Alternatively, Q1 or Q3 can be used as "gates", which allow through only selected ions. Quadrupole Q2 is used in a non-scanning mode, in which it acts as an ion focusing device. All ions pass through Q2 when there is a high vacuum. When a gas is introduced into Q2, incoming ions collide with gas and many of the ions gain sufficient energy to fragment. This is "Collision Induced Dissociation" (CID).

Consider one particular use of the triple quad. Suppose ions are produced in the ion source ($A^+$ $B^+$, $C^+$, $D^+$, etc.). If all of these ions are allowed through Q1, with Q2 and Q3 operating in a scanning mode, then a full mass spectrum is generated (FIG. 11—Mass Spectrum 1). Mass Spectrum 1 shows a spectrum comprising the molecular ions $A^+$ through to $D^+$ and assorted fragment ions.

Now suppose Q1 is set to pass only $A^+$ ions and Q2 is at low pressure. The $A^+$ ions pass through Q2 and Q3 and are detected (FIG. 12—Mass Spectrum 2). The new mass spectrum is now "cleaned", of the other ions ($B^+C^+$, etc.) having been rejected by Q1. Multiple analytes can be detected from the same sample introduced into the mass spectrometer by setting Q1 to scan over a limited series of mass corresponding to particular ion species of the analytes of interest. This is termed "Selective Ion Monitoring".

A triple quadrupole can be used to gain further selectivity, though. It is possible that $A^+$ ions may come from several sources (e.g. several ions could have the same mass to charge ratio of 100 but have different compositions such as $C_7H_{16}$, $C_6H_{12}O$, $C_5H_8O$ etc.). Suppose there are two compositions of $A^+$ ions ($A_1^+$, $A_2^+$) both of the same nominal mass (FIGS. 13 and 14—Mass Spectra 3 and 4). If $A^+$ ions are selected in Q1 and CID is carried out in Q2, a scan of Q3 will give the spectrum shown in FIG. 15—Mass Spectrum 5. This is a "mixed" spectrum.

Suppose it is known that ions $P^+$, $Q^+$ (or even just $P^+$) can unambiguously reveal that $A_1^+$ is present. That is to say, the fragmentation (reaction) $A_1^+ \rightarrow P^+ + Q^+$ is known to occur. Instead of scanning all ions in Q3, it is set to detect only $P^+$ ions. Thus, after leaving the ion source, ions $A^+ B^+ \ldots$ are reduced to just $A^+ (=A_1^+, A_2^+)$ ions going into Q2.

After CID, only fragment ions $P^+$ are selected and these are characteristic of only $A_1^+$. This is said to be "Single or Selective Reaction Monitoring", which is highly selective. In a more generalised sense, the full spectrum of ions entering Q1 (FIG. 11—Mass Spectrum 1) is reduced in Q3 to $P^+$ (FIG. 16—Mass Spectrum 6) and these ions are known to relate only to $A_1^+$.

In some of the ensuing discussions, the examples refer to the use of the mass labels of this invention to identify nucleotides or oligonucleotides. It is equally possible that the labels of this invention can be used with proteins or peptides or other analytes and oligonucleotides are mentioned for the purpose of example. For the purposes of analysing oligonucleotides it is assumed that the mass labels are attached to the oligonucleotide covalently via a cleavable linker. The linker may be cleavable by a variety of mechanisms, including thermal cleavage, chemical cleavage, cone voltage cleavage or photocleavage. In the following discussion of the behaviour of mass labels it is assumed that the labels have been cleaved from their associated nucleic acids during or prior to ionisation. Preferred cleavable linkers and their methods of use are disclosed in GB patent applications GB 9815163.2 and GB 9815164.0. The preferred cleavage process is represented schematically in FIG. 20.

According to the first aspect of this invention the principle of Selected Ion Monitoring (SIM) coupled to Selected Reaction Monitoring (SRM) can be applied to mass marking techniques giving a 2-dimensional detection process. If $A_1^+$ was an ion from a mass label and therefore of known composition and fragmentation pattern then no matter how many ions were produced in the ionisation step, the mass label could be identified without there being any interference from other ions by gating $A^+$ ions in the first quadrupole of a triple quad and then detecting $A_1^+$ fragmentation products, i.e. by gating only $P^+$ ions in the third quadrupole of a triple quadrupole. It would not matter which M/Z range was examined and it is no longer necessary to find "clean" windows in the mass spectrum.

As mentioned above, one aspect of this invention provides mass labels which can be represented schematically by the formula M-L-X. As an example $A_1^+$ could be the molecular ion for the label shown below:

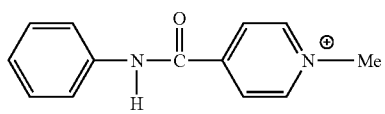

M is thus a benzyl group, L is an amide bond and X is a pyridyl group. The amide bond linking the benzyl ring to the pyridyl ring is particularly susceptible to cleavage by collision. Thus, on collision, $A_1^+$ produces the fragment ion below:

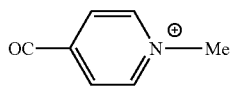

and this would represent $P^+$. Thus, detection of $P^+$ means $A_1^+$ is present and that one of the labels is present. The label has been selectively identified from all other ions and this effectively eliminates "background" contamination. This means that labelled analytes do not need to be exhaustively purified and that the labels do not need to be cleaved and separated from the analyte outside the mass spectrometer. This principle can be generalised to provide a useful class of compounds for use as mass labels, all of which have a general structure M-L-X where M is connected to X via a scissile bond L, such as an amide bond and X is the ion that is detected by SRM. Thus X is analogous to the cleavage product shown above and referred to as $P^+$.

Figure 2:
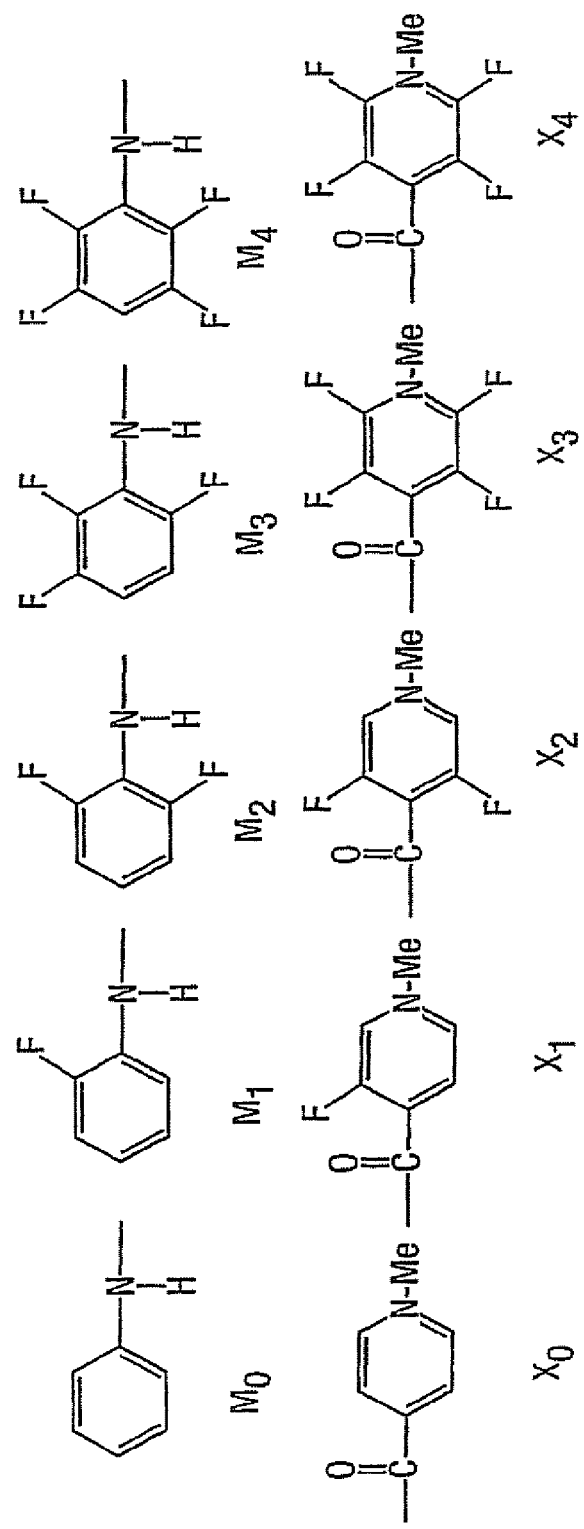
FIG. 2 shows ten fragments comprising five mass normalisation moieties ($M_0$-$M_4$), and five mass marker moieties ($X_0$-$X_4$), for forming a set of labels according to the present invention, in which fluorine atom substituents are employed as mass adjuster moieties.

According to one aspect of this invention the mass label structure illustrated above can be generalised to provide a useful set of mass labels all with the same mass but which are still easily resolved by SRM. Let $M_0, M_1 \ldots M_4$ and $X_0, X_1 \ldots X_4$ be isotopic forms of the halves of M-L-X where L is an amide bond linking M and X. The example above can be used again. If this structure is substituted with fluorine, the components shown in FIG. 2 can be generated. These label components can be combined to form a mass label MX (ignoring the cleavable bond L for the moment) as follows:

Figure 3:
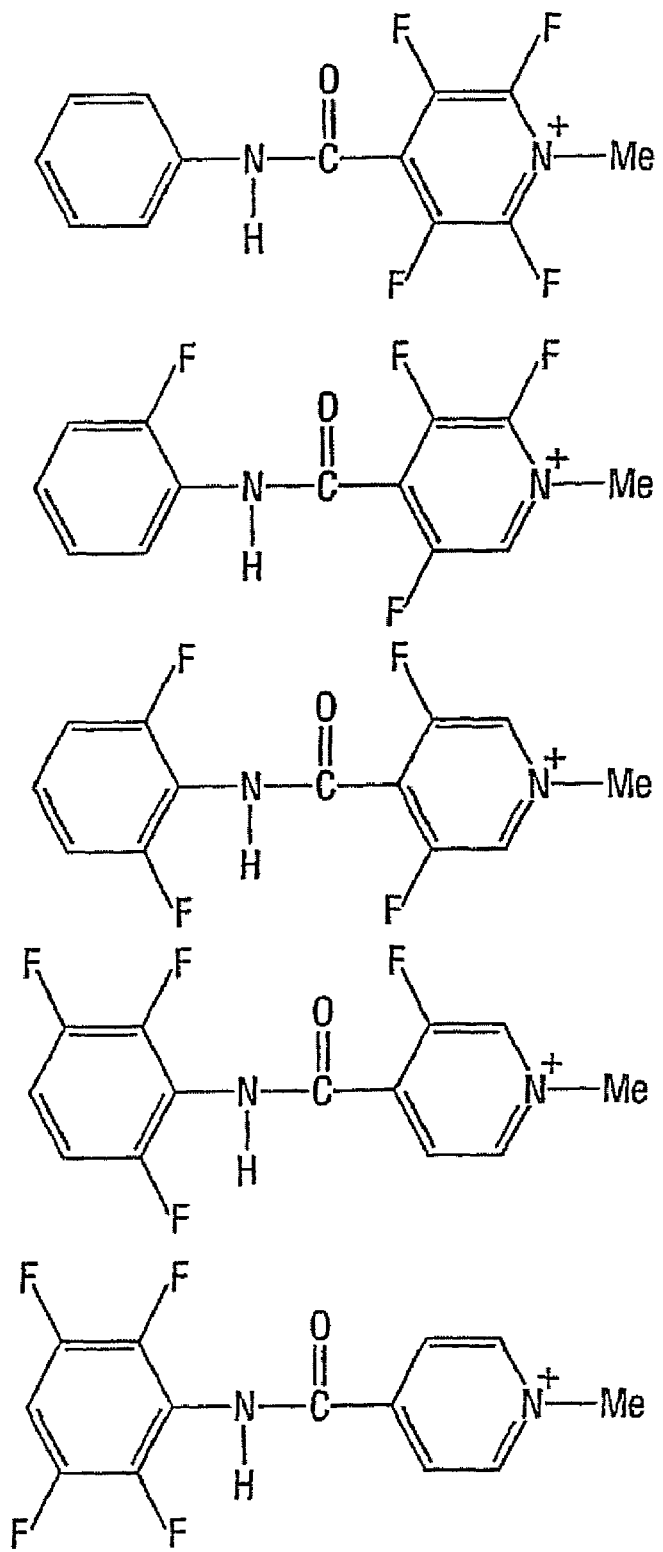
FIG. 3 shows a set of five labels according to the present invention, formed from the mass normalisation moieties and mass marker moieties of FIG. 2.

These five substances have exactly the same mass (FIG. 3). Thus, if a mass label was selected in Q1 of a triple quadrupole, only ions of mass=MmXn (m=0-4, n=4-0) would be selected. Q1 could be set to "look" for only MX ions. If CID is effected in Q2, then Q3 could be set to pass only ions $X_0, X_1, X_2, X_3$ and $X_4$ as shown in FIG. 21.

Therefore, all at the same mass, there would be 5 mass labels selected in Q1 and the cleavage reactions shown below can be identified in Q3. If mass 139 were detected in Q3, it must have come from $M_3X_1$ and so on.

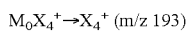

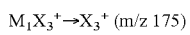

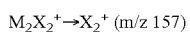

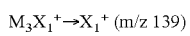

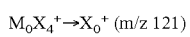

The selection process of this method can be visualised as a two-dimensional mass spectrum shown in FIG. 17—mass spectrum 7.

In an alternative approach, a different set of mass labels can be synthesised. In this mode of analysis SRM is combined with "Selected Ion Monitoring" (SIM). In the SIM mode of analysis, the first quadrupole (Q1) selectively scans over predetermined masses gating only ions with the predetermined masses.

Considering $M_0, M_1, M_2, M_3, M_4$ and $X_0$ from FIGS. 2 and 3 again, these label components can be combined to give 5 labels with different masses, $M_0X_0, M_1X_0, M_2X_0, M_3X_0$ and $M_4X_0$. Now suppose Q1 of a triple quadrupole is set to select these 5 masses, then Q3 need only be set to detect 1 mass ($X_0$) as in FIG. 4. Thus, the mass spectrometer identifies only 1 fixed ion ($X_0$). Since $X_0$ must come from $M_0X_0, M_1X_0, M_2X_0, M_3X_0, M_4X_0$ only and it is known when these have been selected in Q1 then this provides an alternative mode of mass marking. Five different analytes can now be identified by one of five specific "single reactions"

This generates a different 2-dimensional mass spectrum shown in FIG. 18—mass spectrum 8.

The two approaches above can be combined. Suppose $M_0$, $M_1$, $M_2$, $M_3$ are chosen to represent the first base of a dinucleotide. The second base is characterised by $X_0$, $X_1$, $X_2$, $X_3$ to give 16 different mass labels as shown in Table 3 below:

TABLE 3

| Dinucleotide | AA | AC | AG | AT |
|---|---|---|---|---|
| Mass Label | $M_0X_3$ | $M_0X_2$ | $M_0X_1$ | $M_0X_0$ |
| Dinucleotide | CC | CA | CG | CT |
| Mass Label | $M_1X_2$ | $M_1X_3$ | $M_1X_1$ | $M_1X_0$ |
| Dinucleotide | GG | GA | GC | GT |
| Mass Label | $M_2X_1$ | $M_2X_3$ | $M_2X_2$ | $M_2X_0$ |
| Dinucleotide | TT | TA | TC | TG |
| Mass Label | $M_3X_0$ | $M_3X_3$ | $M_3X_2$ | $M_3X_1$ |

Each mass label will have one of 7 different masses which can be selected in the first mass analyser of a tandem instrument. The collision products identified in the second mass analyser will identify the dimer. Thus with 8 mass label components, it is possible to generate 16 mass labels. The full mass 2-dimensional mass spectrum for all of these labels is shown in FIG. 19—mass spectrum 9. Similarly, if 256 mass labels are required, two sets of 16 components, i.e. $M_0$ to $M_{15}$ and $X_0$ to $X_{15}$, would generate sufficient labels, where each label would have one of 31 different masses.

According to another aspect of this invention, it is also possible to generate arrays of sets of mass labels using mass series modifying groups. According to this aspect of the invention a set of labels, where each label in the set has the same mass but can be resolved by SRM, can be expanded into an additional set of labels by linking each member of the set to a mass series modifying group which will shift the mass of each member of the set by a pre-determined amount thus generating a second set of labels whose total mass is different from the first set. Thus two distinct sets of mass label ions would be gated by SIM in the first quadrupole of a mass analyser and the collision products would then be analysed in the third quad by monitoring the same fragment species for both sets of labels. Clearly as many different sets of labels as can be comfortably analysed in a mass spectrometer can be generated by using different mass series modifying groups.

Mass series modifying (S) groups are preferably fragmentation resistant groups such that each S group, when linked to each member of a set of labels, generates a new set of labels that is clearly resolvable from every other in an array of such labels. In this context resolvable means that each set of labels in the array is preferably separated from every other set by approximately 4 daltons at least. This is to ensure that isotope peaks from one label do not overlap in the mass spectrum with those of another label. In preferred embodiments of this aspect of the invention, the S groups are substituted or unsubstituted cyclic groups, such as aryl groups, cycloalkyl groups and heterocyclic groups, preferably linked to the members of a set of SRM resolvable mass marking groups by an ether linkage. Each set in the array may have the same S group, but having a different level of substitution, to ensure that each set is distinct from all other sets. An example of an array of such labels is shown in FIG. 6. In this array, F atoms are used as substituents (adjuster moieties), but other substituents such as methyl groups could be employed. It should be clear that an array of such labels will have very similar effects on the mobility of any associated analyte molecules.

Additional sets of labels could be added to such an array using methyl substituted phenyl groups and also phenyl groups substituted with both methyl and fluoro groups. Methyl groups differ in mass from fluoro groups by just less than 4 daltons and so a significant array of labels could be generated whose effect on the mobility of associated analytes would be minimal.

In other preferred embodiments of this aspect of this invention, the S groups are oligomers or polymers of cyclic groups such as aryl groups, cycloalkyl groups and heterocyclic groups, which may also be substituted. Specifically, preferred S groups are poly-aryl ethers. An example of such an array is shown in FIG. 7.

Figure 5:
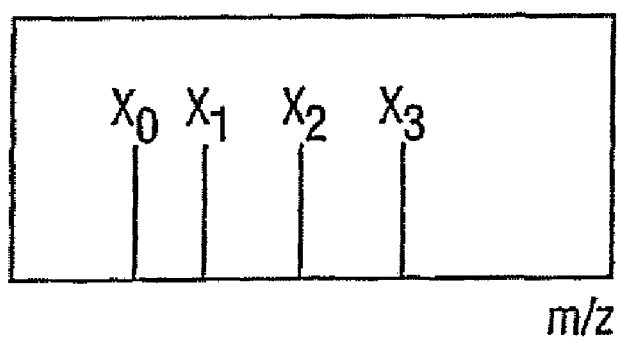
FIG. 5 shows an example of labelling an analyte such as an oligonucleotide with a combination of mass labels; such that the mass label combination has a unique mass spectrum which identifies the analyte.

According to a further aspect of this invention the principles described above can be taken further, by labelling analytes with a distinct combination of the mass labels of the present invention. As mentioned above, this embodiment is termed mixing mode labelling. When any individual analyte of a large number must be identified, for example in combinatorial chemistry, a mixture of labels, e.g. $M_0X_3$, $M_1X_2$, $M_2X_1$, $M_3X_0$ is chosen. The mixture is attached to an analyte, such that a particular quantity of each label is present. For instance, $aM_0X_3 + bM_1X_2 + cM_2X_1 + dM_3X_0$ where $a=b=c=d=1$ (FIG. 5). If equal parts of four mass labels ($a=b=c=d=0.25$) are coupled to an analyte in the same reaction, the chemical joining reaction would not discriminate between them. When an oligonucleotide is labelled, the oligo is mass marked with more than one label per nucleotide or oligonucleotide.

Consider three mass labels of the form shown below in Table 4:

TABLE 4

Figure 8:
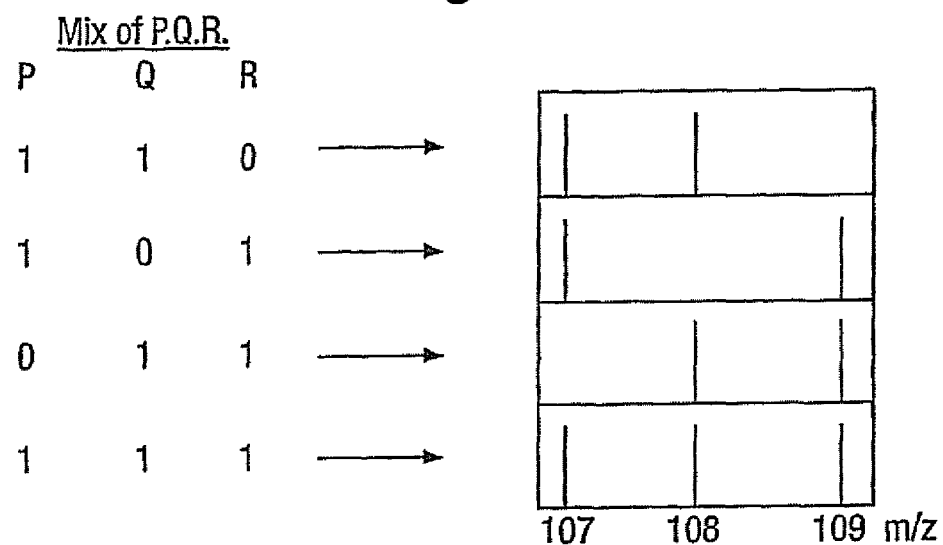
FIG. 8 illustrates the "mixing mode" embodiment of the present invention, showing 4 of the 8 possible unique mass spectra for all combinations of three mass labels P, Q and R when present in relative quantities of 0 or 1.

| Name | Structure | Total Mass | Collision Product Mass (mass marker moiety) |
|---|---|---|---|
| P | 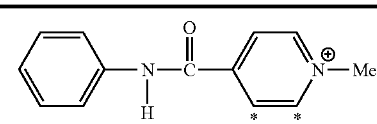 | 199 | 109 |
| Q | 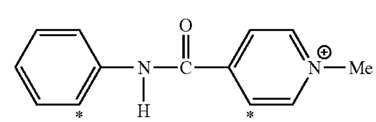 | 199 | 108 |
| R | | 199 | 107 | where "*" can represent $^2H$ or $^{13}C$ isotopes at the position marked. It should be clear that different substituents can be used such as fluorine or methyl groups for example. One mixing mode is such as that shown in FIG. 8. Eight distinct patterns can be generated by a combination of the presence or absence of a distinct labels in a mixture coupled to an analyte molecule.

Consider a different sort of pattern where the ratios of each of five labels are varied when they are coupled to their associated analyte as shown in Table 5 below:

TABLE 5

| P | Q | R | S | T |
|---|---|---|---|---|
| 2 | 2 | 2 | 2 | 2 |
| 2 | 2 | 2 | 1 | 2 |
| 2 | 2 | 2 | 0 | 2 |
| 2 | 2 | 1 | 2 | 2 |
| ... | ... | ... | ... | ... |
| 0 | 0 | 1 | 0 | 2 |
| 0 | 0 | 0 | 2 | 2 |
| 0 | 0 | 0 | 1 | 2 |
| 0 | 0 | 0 | 0 | 2 |

With 4 mass labels, P, Q, R and S, which can be present at 3 different ratios, i.e. none, 1 or 2, there are effectively 3 different entities for each label which means that there are a possible 81 different mass spectral patterns that can be generated. It is preferable that there is also one of these labels whose ratio to the other components remains constant (T), to act as an internal label against which the mass spectrometer data system can compare the relative ratios of P, Q, R and S. This means that with a mixture of 5 labels all 64 combinations of natural nucleotides in a 3-mer oligonucleotide could be identified.

In the above example P, Q, R, S and T can be labels of the form shown in FIG. 3, thus the five labels have the same mass and can be gated from background contaminants in the first quadrupole of a triple quadruple or a Q-TOF instrument, for example. The fragmentation patterns formed as a result of collision with a bath gas in the second quadrupole of a triple quadrupole and detection in the third quadrupole are shown in FIG. 9.

It may be seen that the principle can be extended. In some aspects of the present invention it is desirable to label the 256 possible 4-mers, using the above strategy. It is necessary to generate 7 different labels which can be mixed in all of the possible combinations of ratios shown above. Alternatively, if the labels are of the form shown in FIG. 6 or 7, then 4 sets of 81 codings of the sort shown in the example above can be generated by using the 4 different mass series modifying groups to generate different sets of 5 labels as shown in FIG. 6. This generates sufficient labels to encode all possible 256 4-mers.

The principle of this aspect of the invention can be extended still further. Consider a library of DNA 4-mers comprising all 256 possible combinations of the natural nucleotides. Each 4-mer in the series can be represented as a number from 1 to 256, i.e. AAAA would be 1, and AAAC would be 2 through to TTTT which would be 256.

The numbers 1 to 256 can be represented in a binary form for example in the way numbers could be represented in a memory register of a computer. In a register there is a series of switches which represent the numbers $2^8, 2^7, 2^6, 2^5, 2^4, 2^3, 2^2, 2^1$ and $2^0$. To represent any of the numbers from 1 to 256, the switches are turned on and off so that the sum of the binary powers represents the original decimal number, as shown in Table 6 below:

TABLE 6

|   | $2^8$ | $2^7$ | $2^6$ | $2^5$ | $2^4$ | $2^3$ | $2^2$ | $2^1$ | $2^0$ |
|---|---|---|---|---|---|---|---|---|---|
| 1 | Off | Off | Off | Off | Off | Off | Off | Off | On |
| 2 | Off | Off | Off | Off | Off | Off | Off | On | Off |
| 3 | Off | Off | Off | Off | Off | Off | Off | On | On |
| 4 | Off | Off | Off | Off | Off | Off | On | Off | Off |
| ... | ... | ... | ... | ... | ... | ... | ... | ... | ... |
| 255 | Off | On | On | On | On | On | On | On | On |
| 256 | On | Off | Off | Off | Off | Off | Off | Off | Off |

An analogous representation of these numbers can be achieved with mass label molecules where each switch in the register is represented by the presence or absence of a particular molecule. Thus to identify a 4-mer one could label the 4-mer with the mixture of labels that represents the number that identifies that 4-mer, e.g. if AACG is represented by the number 7, it can be identified by labelling the 4-mer with a mixture of a molecule that represents $2^2$ with molecules that represent $2^1$ and $2^0$.

Practically speaking, these molecules can be represented as a series of molecules based on a core molecule substituted with different numbers of a particular substituent or isotope, e.g. different numbers of a mass adjuster moiety, such as fluorine atoms or different deuterium isotopes. Thus $2^0$ can be represented by the core molecule with no fluorine substituents, $2^1$ can be represented by the core molecule with 1 fluorine substituent and similarly $2^8$ can be represented by the core molecule with 8 fluorine substituents. When these molecules are analysed by mass spectrometry, they can be combined with a complementary component to give 9 isobaric tags which can be analysed in a tandem instrument.

Thus, in the case of the 4-mer AACG, this oligo can be labelled with labels 0, 1 and 2 from the labels shown above. Clearly all other possible 4-mers can be represented in this binary fashion and require only 8 basic labels to identify them such as shown in FIG. 10.

DNA Sequencing Using SRM

The analysis of Sanger Sequencing Ladders can be effected efficiently using mass labels of the form discussed above. Conventional DNA sequencing according to the Sanger methodology uses a DNA polymerase to add numerous dideoxy/deoxynucleotides to an oligonucleotide primer, annealed to a single stranded DNA template, in a template specific manner. Random termination of this process is achieved when terminating nucleotides, i.e. the dideoxynucleotides, are incorporated into the template complement. A "DNA ladder" is produced when the randomly terminated strands are separated on a denaturing polyacrylamide gel or in a capillary. Sequence information is gathered, generally using polyacrylamide gel electrophoresis to separate the terminated fragments by length, followed by detecting the "DNA ladder". In conventional semi-automated and automated DNA sequencers, such as the ABI 377 from Perkin Elmer or MegaBACE from Molecular Dynamics, fluorescent labels $F_1, F_2, F_3, F_4$ are used to identify the four terminating bases A, C, G, T. either through incorporating the fluorescent label into one of the terminating nucleotides or the primer used in the reaction. This ladder is then read by looking for the four dyes passing a detector which scans the gel or a capillary. Other fluorescent detection formats are possible.

Sequencing a Single Template

In the mass spectral method, the fluorescent labels are exchanged for mass labels (e.g. $M_0X_4$; $M_1X_3$; $M_2X_2$; $M_3X_1$; $M_4X_0$ shown in FIG. 3). The dideoxy terminator for Adenine is now labelled with $M_1X_3$. Similarly the dideoxy terminator for Cytosine is now labelled with $M_2X_2$, the terminator for Guanosine is labelled with $M_3X_1$ and the terminator for Thymidine is labelled with $M_4X_0$. As the bands elute from the capillary, they are sprayed, in-line, into the ion source of a suitable tandem mass analyser such as a triple quadrupole where the mass marked nucleic acids are analysed according to an aspect of this invention. Typically, in the ion source the labels are cleaved from the terminating base of each fragment in the ladder and enter the first mass analyser, Q1 of a triple quadrupole. Q1 is set to gate only molecular ions of MX, while Q3 is set to look for labels $X_0$ through $X_4$. It may be desirable that one of the masses, say $X_4$, should be used as an internal standard, viz.; it is always present and $X_0, X_1, X_2$, and $X_3$ are examined in relation to $X_4$.

Figure 4:
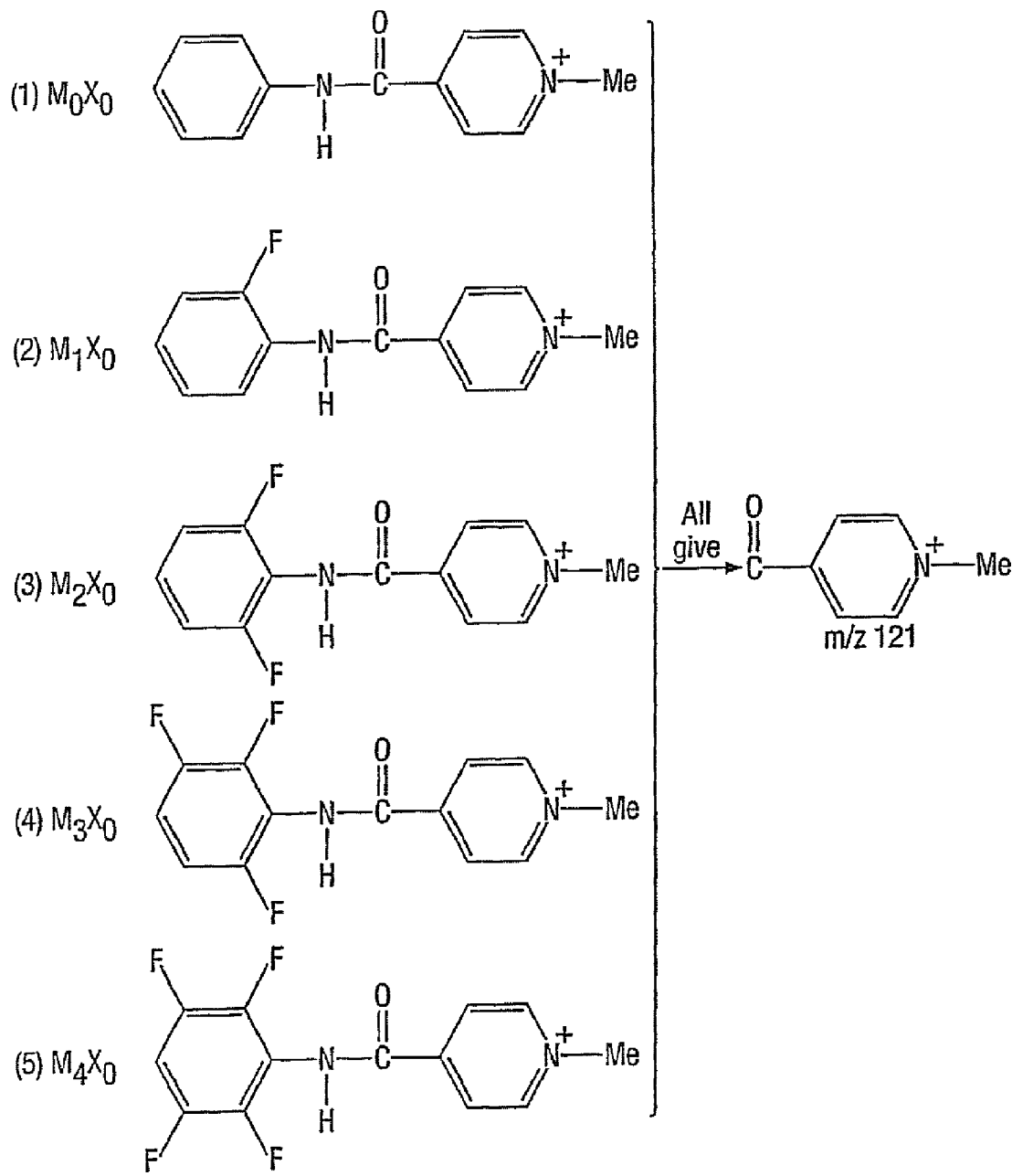
FIG. 4 shows a set of five mass labels according to the present invention in which all the labels have a different mass, but in which all the mass markers of the set have the same mass.

In an alternative approach, the four terminating nucleotides can be labelled with the four labels shown in FIG. 4 so that the dideoxy terminator for Adenine is now labelled with $M_1X_0$. Similarly the dideoxy terminator for Cytosine is now labelled with $M_2X_0$, the terminator for Guanosine is labelled with $M_3X_0$ and the terminator for Thymidine is labelled with $M_4X_0$. The label $M_0X_0$ can be used as an internal standard if desired. In this embodiment, Q1 of a triple quadrupole is set to gate molecular ions of labels $M_4X_0$ through $M_0X_0$, while Q3 is set to look for labels $X_0$.

In addition to nucleotide terminator labelled sequencing, primer labelled sequencing can be performed. Details of primer labelled sequencing, which can employ the mass labels of the present invention are provided in PCT/GB98/02048.

Multiplexed Sequencing of Templates with Mass Labels

The mass labels of this invention permit more than one template to be analysed simultaneously, since many more than four labels can be developed. This means that multiple sets of four labels can be generated to permit analysis of multiple templates according to the methodology described above which is based on the methods devised originally by Sanger. Details regarding the multiplexed sequencing of nucleic acid templates which can employ the mass labels of the present invention are provided in PCT/GB98/02048.

Mass labels of the form shown in FIG. 6 or FIG. 7 can be used to multiplex the analysis of multiple DNA sequences. Each set of five labels, resolvable in the mass spectrometer from every other set by a distinct mass series modifier, can be used to identify a single template, with a spare label remaining for use as a size/quantity standard if desired. However, sets of 4 labels are sufficient for sequencing, and size standards are not essential. It is thus possible, for example, to use the array of 20 labels shown in FIG. 6 to analyse the Sanger reaction products of 5 templates simultaneously.

Gene Expression Profiling

Various methods of analysing populations of complementary DNA derived from poly-adenylated messenger RNA have been developed. A number of these methods are based on detecting different sized amplification or restriction products by electrophoretic separations of amplified cDNA libraries. In general these techniques are based on generating characteristic restriction fragments or amplification products from the members of a complementary DNA (cDNA) library derived from poly-adenylated messenger RNA.

Differential Display (Laing and Pardee, *Science* 257, 967-971, 1992) is the classical method of electrophoresis based gene expression profiling. Developments of the concepts of this technique have been made resulting in improved successors to this technique. Expression profiling methods based on "molecular indexing" using type IIS or type IP restriction endonucleases such as Sibson (PCT/GB93/0145) or Kato (EP 0 735 144 A1) are examples of one class of successors. In particular WO 98/48047 discloses a molecular indexing method based on capillary electrophoresis mass spectrometry (CEMS).

In this method cDNAs are synthesised using anchored and biotinylated poly-thymidine primers, which ensure that all cDNAs are terminated with a short poly-A tail of fixed length. In an "anchored primer" cDNA preparation, poly-A carrying mRNAs are captured and primed using an oligonucleotide of about 18 deoxythymidine residues with one of the three remaining bases at the 3' end to anchor the primer at the end of the poly-A tract. Biotinylation of the primers allows the cDNAs to be immobilised on an avidinated solid phase support. These captured cDNAs may be cleaved with an ordinary type II restriction endonuclease. This leaves a 3' terminal restriction fragment on the solid support while other fragments are washed away. An adapter is ligated to the resulting known sticky-end. The adapter is designed to carry the binding site for a type IIs restriction endonuclease. These enzymes bind their target sequence but cleave the underlying DNA at a defined number of bases away from the binding site. Certain of these enzymes produce a staggered cut; fok1 for example will generate an ambiguous 4 bp sticky-end. If a population of cDNAs is treated with such an enzyme the sticky end will be exposed at the adaptered terminus of each cDNA in the population. A family of adapter molecules is used to probe those 4 exposed bases. With a 4 bp ambiguous sticky-end there are 256 possible candidates. To identify the probes, they are tagged with mass labels using a cleavable linker, so that a unique mass label identifies each of the 256 possible 4 bp adapters. This results in a population of fragments with varying lengths according to where the ordinary type II restriction endonuclease cut them and with one of 256 possible mass labelled adapters at the 5' terminus of the cDNA.

The mass labelled 3' restriction fragments are then separated on the basis of their length, using capillary electrophoresis, followed by analysis of the mass labels ligated to the termini of the cDNA fragments. The CE column feeds directly into an electrospray mass spectrometer or equivalent mass spectrometer. On ionisation in the mass spectrometer the labels cleave from their associated restriction fragments. The quantity of each mass label present in each band, corresponding to a different restriction fragment length, eluting from the capillary electrophoresis column is determined. This process gives a signature for each cDNA that can be used to search a database.

This technique preferably uses 256 mass labels. Using conventional approaches to mass labelling would result in an array of mass tags, separated by about 4 daltons, spanning a mass range of more than a thousand daltons. It is unlikely that an array of such labels could be generated where all the tags had the same effect on the mobility of the associated cDNA restriction fragments. This would mean that complex correction algorithms would have to be used to account for differences in mobility and allow accurate determination of fragment length. The mass markers and associated mass labels of this invention, however, are eminently suitable in the above method, for generating arrays of mass markers whose effect on the mobility of associated analyte molecules is the same, allowing direct determination of fragment length with high sensitivity and excellent signal to noise ratios.

A second class of electrophoretic techniques is based on the use of ordinary type II restriction endonucleases, which are used to introduce primer sequences into cDNA restriction fragments. PCR amplification with labelled primers leads to the generation of distinct restriction fragments, which can be used to identify their associated mRNA. Such methods include that described in U.S. Pat. No. 5,712,126 which discloses a method of introducing adapters into restriction endonuclease digested cDNA fragments which allow selective amplification and labelling of 3' terminal cDNA fragments. Similarly, WO 99/02727, discloses a method of amplifying 3' terminal restriction fragments using solid phase supports and PCR primers which probe the unknown sequence adjacent to a known restriction site. In this technology cDNAs are prepared using biotinylated anchor primers which ensures that all cDNAs are terminated with a short poly-A tail of fixed length and can be immobilised on a solid phase substrate. The poly-T primer may additionally carry a primer sequence at its 5' terminus. The captured cDNAs are then cleaved with an ordinary type II restriction endonuclease. An adapter is ligated to the resulting known sticky-end. The adapter is designed to carry a primer sequence. The resulting double stranded construct is then denatured. The strand that is not immobilised can be washed away if desired. A family of primers complementary to the adapter primer with an overlap of 4 bases into the unknown sequence adjacent to the adapter primer is added to the denatured mixture. With a 4 base overlap there are 256 possible primers. To identify the probes, they are tagged with mass labels using a cleavable linker, so that each of the 256 possible 4 bp overlaps is identified by a label that is uniquely identifiable in a mass spectrometer. This results in a population of fragments with varying lengths according to where the ordinary type II restriction endonuclease cut them and with one of 256 possible mass labelled primers at the 5' terminus of the cDNA. The cycle of denaturing and primer extension can be performed as many times as desired. If only the adapter primer sites are used, a linear amplification can be performed. This causes smaller distortion of cDNA quantification than exponential amplification. If exponential amplification is desired then the poly-T oligos used to trap the mRNAs must carry a primer site as well. Exponential amplification may be desirable if small tissue samples must be analysed despite the potential for distortions of cDNA frequencies.

Again, the mass labelled 3' restriction fragments are separated on the basis of the length, using capillary electrophoresis, of the restriction fragments followed by analysis of the mass labels at the termini of the cDNA fragments. This technique, like that disclosed in WO 98/48047 is preferably practised with 256 mass labels and would thus benefit in the same way from the advantageous features of the mass labels of this invention.

Thus, in a further aspect of this invention, there is provided a method of analysis comprising the steps of:
1. Providing a population of mass labelled nucleic acid fragments of different lengths, where the mass labels are indicative of a feature of the labelled nucleic acids.
2. Separating the labelled fragments on the basis of their size
3. Detaching the mass labels from the labelled fragments
4. Detecting the mass labels in a mass spectrometer.

In certain embodiments of this aspect of the invention, the assay determines the sequence of nucleic acid or a series of nucleic acids. In sequencing embodiments based on the generation of Sanger ladders the mass label identifies the terminating nucleotide of each fragment and each fragment is identified by a set of four labels. In Sanger sequencing embodiments the labels are introduced as mass labelled primers or labelled terminating nucleotides.

In other embodiments of this aspect of the invention, the assay is used to determine the identity and quantity of expressed RNA molecules. In preferred embodiments, the mass labelled nucleic acids are generated according to the methods disclosed in WO 98/48047 or WO 99/02727. In embodiments using these methods mass labels are introduced into the nucleic acid fragments by ligation of mass labelled adapters or by extension of mass labelled primers, respectively. For one of ordinary skill in the art, it should be clear that other methods of gene expression profiling based on the size of nucleic acid fragments, such as those disclosed in PCT/GB93/0145, EP-A-0 735 144 or U.S. Pat. No. 5,712,126, can be adapted for use with the labels of this invention.

In preferred embodiments of this invention the step of separating the analytes on the basis of size is carried out using capillary electrophoresis or high performance liquid chromatography, using, for example, systems such as those provided by Transgenomic, Inc. (San Jose, Calif., USA.) and disclosed in U.S. Pat. No. 5,585,236, U.S. Pat. No. 5,772,889 and other applications. Preferably the separation is performed on-line with a mass spectrometer.

In preferred embodiments, the step of detaching the mass labels from their associated analytes takes place within the ion source of the mass spectrometer. Linkers that allow a mass label to be easily cleaved from its associated analyte in a mass spectrometer ion source are disclosed in PCT/GB98/00127. Compounds that improve the sensitivity of detection of a mass label by mass spectrometry are disclosed in PCT/GB98/00127.

For one of ordinary skill in the art, it should be clear that other sizing assays could be adapted for use with the mass labels of this invention, including, for example, the multiplexed genotyping assay disclosed by Grossman P. D. et al. in Nucleic Acids Research 1994 Oct. 25; 22(21):4527-34. This assay would benefit greatly from the ability to multiplex to higher orders and still resolve the size of fragments easily.

Protein Expression Profiling and 2-Dimensional Gel Electrophoresis

Techniques for profiling proteins, that is to say cataloguing the identities and quantities of all the proteins expressed in a tissue, are not well developed in terms of automation or throughput. The classical method of profiling a population of proteins is by two-dimensional electrophoresis (R. A. Van Bogelen, E. R. Olson, "Application of two-dimensional protein gels in biotechnology", Biotechnol. Ann. Rev., 1:69-103, 1995). In this method a protein sample extracted from a biological sample is separated on a narrow gel strip. This first separation usually separates proteins on the basis of their iso-electric point. The entire gel strip is then laid against one edge of a rectangular gel, such as a polyacrylamide gel. The separated proteins in the strip are then electrophoretically separated in the second gel on the basis of their size, e.g. by Sodium Dodecyl Sulphate Polacrylamide Gel Electrophoresis (SDS PAGE). This methodology is slow and very difficult to automate. It is also relatively insensitive in its simplest incarnations. Once the separation is complete the proteins must be visualised. This typically involves staining the gel with a reagent that can be detected visually or by fluorescence. Radiolabelling and autoradiography are also used. In other methods fluorescent dyes may be covalently linked to proteins in a sample prior to separation. Covalent addition of a dye can alter the mobility of a protein and so this is sometimes less preferred, particularly if comparisons are to be made with public databases of 2-dimensional gel images. Having visualised the proteins in a gel it is usually necessary to identify the proteins in particular spots on the gel. This is typically done by cutting the spots out of the gel and extracting the proteins from the gel matrix. The extracted proteins can then be identified by a variety of techniques. Preferred techniques involve digestion of the protein, followed by microsequencing. A number of improvements have been made to increase resolution of proteins by 2-D gel electrophoresis and to improve the sensitivity of the system. One method to improve the sensitivity of 2-D gel electrophoresis and its resolution is to analyse the protein in specific spots on the gel by mass spectrometry (Jungblut P., Thiede B. "Protein identification from 2-D gels by MALDI mass spectrometry", Mass Spectrom. Rev. 16, 145-162, 1997). One such method is in-gel tryptic digestion followed by analysis of the tryptic fragments by mass spectrometry to generate a peptide mass fingerprint. If sequence information is required, tandem mass spectrometry analysis can be performed.

At present 2-D analysis is a relatively slow "batch" process. It is also not very reproducible and it is expensive to analyse a gel. Since most of the costs in a gel based analysis are in the handling of each gel it would be desirable to be able to multiplex a number of samples on a 2-D gel simultaneously. If it were possible to label the proteins in different samples with a different, independently detectable tag, then the proteins in each sample could be analysed simultaneously on the same gel. This would be especially valuable for studies where it is desirable to follow the behaviour of the same proteins in a particular organism at multiple time points, for example in monitoring how a bacteria responds to a drug over a predetermined time course. Similarly comparing biopsy material from multiple patients with the same disease with corresponding controls would be desirable to ensure that the same protein from different samples would end up at the same spot on the gel. Running all the samples on the same gel would allow different samples to be compared without having to be concerned about the reproducibility of the separation of the gel. To achieve this requires a series of labels whose effect on the mobility of the proteins in different samples will be the same, so that a particular protein which is labelled with a different label in each sample will still end up at the same position in the gel irrespective of its label.

More recently attempts have been made to exploit mass spectrometry to analyse whole proteins that have been fractionated by liquid chromatography or capillary electrophoresis (Dolnik V. "Capillary zone electrophoresis of proteins", Electrophoresis 18, 2353-2361, 1997). In-line systems exploiting capillary electrophoresis mass spectrometry have been tested. The analysis of whole proteins by mass spectrometry, however, suffers from a number of difficulties. The first difficulty is the analysis of the complex mass spectra resulting from multiple ionisation states accessible by individual proteins. The second major disadvantage is that the mass resolution of mass spectrometers is at present quite poor for high molecular weight species, i.e. for ions that are greater than about 4 kilodaltons in mass so resolving proteins that are close in mass is difficult. A third disadvantage is that further analysis of whole proteins by tandem mass spectrometry is difficult as the fragmentation patterns for whole proteins are extremely complex and difficult to interpret.

PCT/GB98/00201 and PCT/GB99/03258, describe methods of characterising complex mixtures of proteins by isolating C-terminal peptides from the proteins in the mixtures and analysing them by mass spectrometry. The methods described can be used to determine whether proteins are present or absent in a sample but would not give comparative data between samples. The methods do not describe techniques for analysis of multiple samples simultaneously, which would be necessary for quantitative comparison of protein expression levels in multiple samples.

EP-A-0 594 164 describes a method of isolating a C-terminal peptide from a protein in a method to allow sequencing of the C-terminal peptide using N-terminal sequencing reagents. In this method the protein of interest is digested with an endopeptidase which cleaves at the C-terminal side of lysine residues. The resultant peptides are reacted with DITC polystyrene, which reacts with all free amino groups. N-terminal amino groups that have reacted with the DITC polystyrene can be cleaved with trifluoroacetic acid (TFA) thus releasing the N-terminus of all peptides. The epsilon-amino group of lysine is not cleaved, however, and all non-terminal peptides are thus retained on the support and only C-terminal peptides are released. According to this document, the C-terminal peptides are recovered for micro-sequencing.

Nature Biotechnology 17: 994-999 (1999) discloses the use of "isotope encoded affinity tags" for the capture of peptides from proteins to allow protein expression analysis. In this article, the authors describe the use of a biotin linker, which is reactive to thiols to capture peptides with cysteine in them. A sample of protein from one source is reacted with the biotin linker and cleaved with an endopeptidase. The biotinylated cysteine containing peptides can then be isolated on avidinated beads for subsequent analysis by mass spectrometry. Two samples can be compared quantitatively by labelling one sample with the biotin linker and labelling the second sample with a deuterated form of the biotin linker. Each peptide in the samples is then represented as a pair of peaks in the mass spectrum where the relative peak heights indicate their relative expression levels.

The method in this paper has a number of limitations. Of the various limitations to this "isotope encoding" method, the first is the reliance on the presence of thiols in a protein—many proteins do not have thiols while others have several. In a variation on this method, linkers may be designed to react with other side chains such as amines, but since many proteins contain more than one lysine residue, multiple peptides per protein will be isolated in this approach. It is likely that this would not reduce the complexity of the sample sufficiently for analysis by mass spectrometry. A sample that contains too many species is likely to suffer from "ion suppression" in which certain species ionise preferentially over other species which would normally appear in the mass spectrum in a less complex sample. In general, capturing proteins by their side chains may give either too many peptides per protein or certain proteins will be missed altogether.

The second limitation of this approach is in the method used to compare the expression levels of proteins from different samples. Labelling each sample with a different isotope variant of the affinity tag results in an additional peak in the mass spectrum for each peptide in each sample, which means that if two samples are analysed together there will be twice as many peaks in the spectrum. Similarly, if three samples are analysed together, the spectrum will be three times more complex than for one sample alone. It might be feasible to attempt the comparison of two or three samples by this approach but this may well be the limit as the ever increasing numbers of peaks will increase the likelihood that two different peptides will have overlapping peaks in the mass spectrum.

A further limitation reported by the authors of the above paper is the mobility change caused by the tags. The authors report that peptides labelled with the deuterated biotin tag elute slightly after the same peptide labelled with the undeuterated tag.

In view of the above, a further aim of the present invention it is an to provide an improved method of determining the identity and relative quantities of polypeptides in a number of samples of complex polypeptide mixtures simultaneously. It is a further aim of this aspect of the invention to ensure that all proteins are represented in the analysis. It is also an aim of this aspect of the invention to provide mass labels and techniques which allow multiple samples to be analysed simultaneously and quantitatively without increasing significantly the complexity of the mass spectrum when compared to the spectrum that would be obtained from a single sample alone. It is a final aim of this aspect of the invention to provide labels which have the same effect on the mobility of the labelled peptide, so that samples of the same peptide labelled with different tags will co-elute after a chromatographic separation.

Thus, a further preferred embodiment of this invention provides a method of analysing a protein sample containing more than one protein, the method comprising the steps of:

1. Labelling peptides, polypeptides and/or proteins in the sample with at least one discretely resolvable mass label from the sets and arrays of this invention, such that each peptide, polypeptide and/or protein is labelled with a label or combination of labels unique to that protein
2. Analysing the labelled peptides, polypeptides and/or proteins by mass spectrometry, preferably according to an aspect of this invention e.g. tandem mass spectrometry, to detect the labels attached to the proteins. The labelled peptides in the sample may then be identified and their relative expression levels determined.

It is preferred that multiple samples are subjected to the above process. It is further preferred that for each of a number of samples, prior to labelling step (1) above, peptides are isolated from polypeptides in the mixture using a cleavage agent, especially a sequence specific cleavage agent. After labelling step (1), the samples may be pooled, if desired. Optionally, after labelling step (1) and/or pooling the samples, the peptides polypeptides and/or proteins in the sample or samples may be separated, by gel electrophoresis, iso-electric focusing, liquid chromatography or other appropriate means, preferably generating discrete fractions. These fractions may be bands or spots on a gel or liquid fractions from a chromatographic separation. Fractions from one separation may separated further using a second separation technique. Similarly further fractions may be fractionated again until the proteins are sufficiently resolved for the subsequent analysis steps.

This aspect of the invention thus provides a further application of the labels and methods of this invention described above. A set or array of labels of the present invention can be used to increase the throughput of a 2-D gel electrophoresis analysis of the proteins in an organism. Each of the mass labels alters the mobility of its associated protein in the same way but is still independently detectable. In known uses of mass spectrometry to analyse proteins from a 2-D gel, such as peptide mass fingerprinting, it is required that the proteins be extracted from the gel and be purified to remove detergents such as SDS and other contaminants from the gel. The labels of this invention allow relatively unpurified extract of proteins from the gel to be introduced directly into the mass spectrometer and the associated labels can then be identified by the methods of this invention in a background of contaminating material.

In a particularly preferred embodiment of this aspect of the invention multiple samples are subjected to the following process:

1. for each of a number of samples, isolating peptides from polypeptides in the mixture using sequence specific cleavage reagents;
2. labelling the isolated peptides in each sample with the labels of this invention such that each sample is identified by a unique label;
3. pooling the labelled samples;
4. optionally separating the pooled and labelled peptides chromatographically or electrophoretically;
5. analysing these labelled samples by tandem mass spectrometry to identify the labelled peptides in the sample and determine their relative expression levels.

Another preferred embodiment of this aspect of the invention provides a method of analysing a series of protein samples each sample containing more than one protein, the method comprising the steps of:

1. Covalently reacting the proteins of each of the samples with at least one discretely resolvable mass label from the sets and arrays of this invention, such that the proteins of each sample are labelled with one or more mass labels that are different from the labels reacted with the proteins of every other sample.
2. Pooling the mass labelled samples.
3. Separating the pooled samples by gel electrophoresis, iso-electric focusing, liquid chromatography or other appropriate means to generate discrete fractions. These fractions may be bands or spots on a gel or liquid fractions from a chromatographic separation. Fractions from one separation may separated further using a second separation technique. Similarly further fractions may be fractionated again until the proteins are sufficiently resolved for the subsequent analysis steps.
4. Analysing the fractions by mass spectrometry, preferably according to an aspect of this invention, to detect the labels attached to the proteins.

A still further preferred embodiment of this aspect of the present invention provides a method of identifying a protein in a sample containing more than one protein, the method comprising the steps of:

1. Covalently reacting the proteins of the sample with at least one discretely resolvable mass label from the sets and arrays of this invention.
2. Separating the proteins by gel electrophoresis, iso-electric focusing, liquid chromatography or other appropriate means to generate discrete fractions. These fractions may be bands or spots on a gel or liquid fractions from a chromatographic separation. Fractions from one separation may separated further using a second separation technique. Similarly further fractions may be fractionated again until the proteins are sufficiently resolved for the subsequent analysis steps.
3. Digesting the proteins in the fraction with a sequence specific cleavage reagent.
4. Optionally reacting the proteins in the sample with an additional mass label
5. Analysing the digested fractions by liquid chromatography mass spectrometry where the elution time of mass marked peptides from the liquid chromatography column step is determined by detecting the mass labels attached to the peptides. A mass spectrometry analysis is performed, preferably according to an aspect of this invention, to detect the labels attached to the proteins.
6. Comparing the elution profile of the labelled peptides from the liquid chromatography mass spectrometry analysis of step 5 with profiles in a database to determine whether the protein has been previously identified.

A yet further preferred embodiment of this aspect of the present invention provides a method of identifying a protein from a series of protein samples each sample containing more than one protein, the method comprising the steps of:

1. Covalently reacting the proteins of each of the samples with at least one discretely resolvable mass label from the sets and arrays of this invention, such that the proteins of each sample are labelled with one or more mass labels that are different from the labels reacted with the proteins of every other sample.

2. Pooling the mass labelled samples.
3. Separating the proteins by gel electrophoresis, iso-electric focusing, liquid chromatography or other appropriate means to generate discrete fractions. These fractions may be bands or spots on a gel or liquid fractions from a chromatographic separation. Fractions from one separation may separated further using a second separation technique. Similarly further fractions may be fractionated again until the proteins are sufficiently resolved for the subsequent analysis steps.
4. Digesting the proteins in the fraction with a sequence specific cleavage reagent to generate characteristic peptides for each protein in the sample.
5. Optionally reacting the proteins in the sample with an additional mass label.
6. Analysing the digested fractions by liquid chromatography mass spectrometry where the elution time of mass marked peptides from the liquid chromatography column step is determined by detecting the mass labels attached to the peptides. A mass spectrometry analysis is performed, preferably according to an aspect of this invention, to detect the labels attached to the proteins.
7. Comparing the elution profile of the labelled peptides from the liquid chromatography mass spectrometry analysis of step 6 with profiles in a database to determine whether the protein has been previously identified.

Step 1 of the above preferred embodiments of this invention involves covalently reacting a mass label of this invention to the reactive side chains of a population of proteins. It is well known in the art that the reactive side-chain functionalities can be selectively reacted. Reactive side-chains include lysine, serine, threonine, tyrosine and cysteine. Cysteine is often cross-linked with itself to form disulphide bridges. For the purposes of this invention it is not essential that these bridges be broken but cysteine side chains can be highly reactive and may be readily reacted with a variety of reagents. If disulphide bridges are present, these can be broken by reducing the disulphide bridge to a pair of thiols with mercaptethanol. Thiols can be selectively capped by iodoacetate (Aldrich) under mildly basic conditions which promote the formation of a thiolate ion (Mol. Microbiol. 5: 2293, 1991). An appropriate mild base is a carbonate. For the purposes of this invention, a mass label of this invention whose reactive functionality is an iodoacetyl group can be reacted with the thiols of an analyte protein. In other embodiments the population of proteins may be treated with a mass marker whose reactive functionality is an isocyanate group. Isocyanates will react almost exclusively with the alpha-amino group at the N-terminus of the proteins and with any lysine epsilon-amino groups, i.e. with primary amines under mild conditions, i.e. at room temperature in a neutral solvent to give a urea derivative. These reagents can also be made to react with any hydroxyl bearing side-chains, such as serine, threonine and tyrosine side chains, at higher temperatures in the presence of an appropriate catalyst such as pyridine or a tin compound such as dibutyl stannyl laurate to give a urethane derivative. In an alternative embodiment the population of proteins can be treated with a mass marker whose reactive functionality is a silyl group such as chlorosilane. These compounds react readily with most reactive functional groups. Amine derivatives are not stable under aqueous conditions and so can be hydrolysed back to the free amine if that is desired. Sulphonyl chlorides can also be used as a reactive group on a mass label to selectively react the mass label with free amines such as lysine. Carboxylic acid side chains could also be reacted with the labels of this invention although it is usually necessary to activate these side chains to ensure that they will react. Acetic anhydride is commonly used for this purpose. This forms mixed anhydrides at free carboxylic acids which can then be reacted with a nucleophilic functionality such as amine.

The above specific embodiments are intended only as examples illustrating preferred methods of selectively reacting side-chain functionalities with mass labels. A wide variety of reactive groups are known in the art and many of these can be used to complete the first steps of these aspects of this invention. It may also be desirable to react more than one type of side chain of the proteins in a sample with different mass labels. If multiple samples are to be analysed simultaneously then two or more labels can be used to label each sample. This allows more information to be derived from each protein to aid in its identification.

In step 3 and step 4 of the latter two embodiments of this aspect of the invention, the C-terminally modified proteins are then treated with a sequence specific cleavage agent. In some embodiments sequence specific endoproteinases such as trypsin, chymotrypsin, thrombin or other enzymes may be used. Cleavage agents may alternatively be chemical reagents. These are preferably volatile to permit easy removal of unreacted reagent. Appropriate chemical cleavage reagents include cyanogen bromide which cleaves at methionine residues and BNPS-skatole which cleaves at tryptophan residues (D. L. Crimmins et al., Anal. Biochem. 187: 27-38, 1990).

In the above preferred embodiments of this aspect of the invention, the step of fractionating the proteins is preferably effected by performing 2-dimensional gel electrophoresis, using iso-electric focusing in the first dimension and SDS PAGE in the second dimension. The gel is then visualised to identify where proteins have migrated to on the gel. The spots can then be excised from the gel and the proteins are then extracted from the excised gel spot. These extracted proteins may then be analysed directly by electrospray mass spectrometry or some other suitable ionisation procedure. Alternatively further fractionation may be performed in-line with the mass spectrometer such as HPLC mass spectrometry.

In step 3 and step 4 of the latter two preferred embodiments of this aspect of the invention, the digested proteins are optionally reacted with an additional mass label of this invention. This is of more significance to the latter preferred embodiment of this invention, where multiple samples are analysed simultaneously. Most enzymatic digestions and some of the chemical cleavage methods leave free amines on the resultant peptides of the digested fractionated proteins which can be reacted with a mass label. This means that the same label will appear on all peptides and can be detected selectively to maximise the sensitivity of this analysis.

In step 6 and step 7 of the latter two preferred embodiments of this aspect of the invention, the elution profile of the peptides generated by digesting the fractionated proteins is used to search a pre-formed database to determine whether the proteins have been previously identified. The peptides eluting from the liquid chromatography column into a mass spectrometer may be further analysed by tandem mass spectrometry to determine sequence information which can be used to identify proteins. Peptide sequence data can be used to search a protein sequence database or can translated into nucleic acid sequence data to search nucleic acid sequence databases.

Isolation of Post-Translationally Modified Peptides

Carbohydrates are often present as a post-translational modification of proteins. These carbohydrates often have carbonyl groups. Carbonyl groups can be tagged allowing proteins bearing such modifications to be detected or isolated. Biocytin hydrazide (Pierce & Warriner Ltd, Chester, UK) will react with carbonyl groups in a number of carbohydrate species (E. A. Bayer et al., Anal. Biochem. 170, 271-281, "Biocytin hydrazide—a selective label for sialic acids, galactose, and other sugars in glycoconjugates using avidin biotin technology", 1988). Proteins bearing carbohydrate modifications in a complex mixture can thus be biotinylated. The protein mixture may then be treated with an endoprotease, such as trypsin, to generate peptides from the proteins. Biotinylated, hence carbohydrate modified, peptides may then be isolated using an avidinated solid support. A series of samples may be treated in this way and the peptides obtained may be reacted with the mass labels of this invention, such that peptides from each sample bear a mass label or combination of mass labels relatable to the peptide or peptides from that sample. Preferably peptides from each sample bear a different mass label. These mass tagged carbohydrate-bearing peptides may then be analysed by liquid chromatography tandem mass spectrometry.

A number of research groups have reported on the production of antibodies, which bind to phosphotyrosine residues in a wide variety of proteins (see for example A. R. Frackelton et al., Methods Enzymol. 201, 79-92, "Generation of monoclonal antibodies against phosphotyrosine and their use for affinity purification of phosphotyrosine-containing proteins", 1991 and other articles in this issue of Methods Enzymol.). This means that a significant proportion of proteins that have been post-translationally modified by tyrosine phosphorylation may be isolated by affinity chromatography using these antibodies as the affinity column ligand.

These phosphotyrosine binding antibodies can be used in the context of this invention to isolate peptides containing phosphotyrosine residues. Thus proteins in a complex mixture may be treated with a sequence specific endopeptidase to generate free peptides. These may then be passed through an anti-phosphotyrosine antibody column, which will retain peptides containing a phosphotyrosine group. A series of samples may be treated in this way and the peptides obtained may be reacted with the mass tags of this invention, such that peptides from each sample bear a mass label or combination of mass labels relatable to the peptide or peptides from that sample. Preferably peptides from each sample bear a different mass label. These mass labelled phosphotyrosine-bearing peptides may then be analysed by liquid chromatography tandem mass spectrometry.

Isolation of Terminal Peptides from Proteins

A preferred method of protein expression profiling according to the present invention is to isolate only one peptide from each protein in the sample. Provided that the isolated peptide fragment is of sufficient length, the fragment will be specific to its parent protein. In the first step of this aspect of the present invention, peptides are isolated from each protein in each of a number of samples of complex protein mixtures. In some embodiments of this aspect it is preferred that terminal peptides are isolated. Isolation of terminal peptides ensures that at least one and only one peptide per protein is isolated. Methods for isolating peptides from the termini of polypeptides are discussed in PCT/GB98/00201 and PCT/GB99/03258.

Thus, this aspect of the present invention provides a method of protein profiling, which method comprises:

(a) treating a sample comprising a population of a plurality of polypeptides with a cleavage agent which is known to recognise in polypeptide chains a specific amino acid residue or sequence and to cleave at a cleavage site, whereby the population is cleaved to generate peptide fragments;

(b) isolating a population of peptide fragments bearing as a reference terminus the N-terminus or the C-terminus of the polypeptide from which they were fragmented, each peptide fragment bearing at the other end the cleavage site proximal to the reference terminus;

(c) prior to or after isolating the peptide fragments, labelling each reference terminus of the polypeptides with a mass label, or a combination of mass labels from a set or an array of mass labels of the present invention, wherein each reference terminus is relatable to its label or combination of labels; and (d) determining by mass spectrometry a signature sequence of one or more of the isolated fragments, which signature sequence is the sequence of a pre-determined number of amino acid residues running from the cleavage site;

wherein a signature sequence characterises each polypeptide.

An alternative preferred method provided by this aspect of the present invention makes use of a second cleavage agent to generate further fragments, which may themselves be identified and used to characterise their parent polypeptide or protein. This method comprises:

(a) contacting a sample comprising one or more polypeptides with a first cleavage agent to generate polypeptide fragments;

(b) isolating one or more polypeptide fragments, each fragment comprising the N-terminus or the C-terminus of the polypeptide from which it was fragmented;

(c) prior to or after isolating the polypeptide fragments, labelling each terminus of the polypeptides with a mass label, or a combination of mass labels from a set or an array of mass labels of the present invention, wherein each terminus is relatable to its label or combination of labels; and (d) identifying the isolated fragments by mass spectrometry;

(e) repeating steps (a)-(d) on the sample using a second cleavage agent that cleaves at a different site from the first cleavage agent; and (f) characterising the one or more polypeptides in the sample from the fragments identified in steps (d) and (e).

In both of the above methods, the step of labelling the reference termini can take place before or after isolating the fragments and can also take place before the fragments are cleaved from their parent polypeptides or proteins, if desired.

Regarding the isolation of peptide fragments, in preferred embodiments of this aspect of the present invention, terminal peptides may be isolated from a complex mixture of proteins using a method, comprising the steps of:

1. Digesting the complex mixture of proteins completely with a Lys-C specific cleavage enzyme, i.e. a reagent that cuts at the peptide bond immediately adjacent to a lysine residue on the C-terminal side of that residue.

2. Contacting the resultant peptides with an activated solid support that will react with free amino groups.

3. Optionally reacting the captured peptides with a bifunctional reagent, which has at least one amine reactive functionality.

4. Contacting the captured peptides with a reagent that which cleaves at the alpha amino groups of each peptide on the support. All peptides that are not C-terminal will have a lysine residue covalently linking them to the solid support. Thus free C-terminal peptides are selectively released.

5. Optionally contacting the released peptides with a second solid support that will react with the second reactive functionality of the bifunctional reagent used in step 3 to capture any peptides that did not react properly with the first support.

6. Recovering the peptides remaining free in solution.

In preferred embodiments of, this method, the proteins in the complex mixture are denatured, reduced and treated with a reagent to cap thiols in the proteins. Typical protocols involve denaturing the proteins in a buffer at pH 8.5 with a high concentration of guanidine hydrochloride (6-8 M), as a denaturation reagent, in the presence of an excess of mercaptoethanol or dithiothreitol, as reducing agents, and an excess of a capping agent such as vinylpyridine.

In step 1 of this method, the complex mixture of proteins is completely digested with a Lys-C specific cleavage enzyme, which may be, for example, endopeptidase Lys-C from Lysobacter enzymogenes (Boehringer Mannheim).

In step 2 of this method, the resultant peptides are contacted with a solid support that reacts with amines. In preferred embodiments the solid phase support is derivatised with an isothiocyanate compound. In one embodiment the peptide population is reacted with isothiocyanato glass (DITC glass, Sigma-Aldrich Ltd, Dorset, England) in the presence of a base. This captures all peptides to the support through any free amino groups.

Step 3 is optional but preferred. It may be difficult to guarantee that all non-C-terminal peptides will react completely with the first solid support at both the lysine side-chain amino-group and the N-terminal alpha amino-group. Peptides that react only through the lysine side-chain amino groups will remain attached to the support in subsequent steps. Peptides that react only through their alpha-amino group will be cleaved from the support along with C-terminal peptide. This step allows the non-C-terminal peptides to be distinguished from C-terminal peptides. In this optional step, the bifunctional reagent may be N-succinimidyl[4-vinylsulphonyl]benzoate (SVSB from Pierce & Warriner Ltd., Chester, UK). This compound comprises an amine-reactive N-hydroxysuccinimide ester linked to a thiol-reactive vinyl sulphone moiety. The compound reacts very easily with amines via the ester functionality without reaction of the vinyl sulphone and can be separately reacted with thiols at a later stage. Thus the SVSB is reacted with any free amines on the support under slightly basic conditions. In the presence of a large excess of the SVSB compound and given that the peptides on the support are immobilised, the SVSB will react with the peptides only through the succinimide functionality leaving the vinyl sulphone moiety free for further reaction. In alternative embodiments, any unreacted amines may be reacted with biotin coupled to an amine reactive functionality such as N-hydroxysuccinimide (NHS) biotin (Sigma-Aldrich Ltd, Dorset, England). This allows incompletely reacted peptides to be captured later on avidinated beads or on an avidinated resin in an affinity capture column.

In step 4 of this method the captured peptides are contacted with a reagent that cleaves at the alpha amino groups of each peptide on the support. In embodiments where DITC glass is used as the amine reactive support, the peptides are treated with an appropriate volatile acid such as trifluoroacetic acid (TFA) which cleaves the N-terminal amino acid from each peptide on the support. All peptides that are not C-terminal will have a lysine residue covalently linking them to the solid support. Thus free C-terminal peptides are selectively released.

The optional step 5 is preferred especially if the optional step 3 is performed. The non-C-terminal peptides that do not react completely with the amine reactive support are removed by this step. If SVSB is used to tag non-C-terminal peptides that only reacted through their alpha-amino groups they will have a reactive functionality available which will allow them to be reacted with a solid support derivatised with an appropriate nucleophile, preferably a thiol. If DITC glass is used in step 4, which is preferred, then the peptides may be released from support using TFA. The released peptides may be recovered as trifluoroacetate salts by evaporating the TFA away. The peptides may then be resuspended in a buffer with a pH of about 7 or just in an appropriate neutral solvent such as dimethylformamide, dimethylsulphoxide or a mixture of water and acetone. The peptides are then added to the thiol derivatised support. At pH 7 the remaining vinyl functionality on the SVSB treated peptides should react almost exclusively with the thiol support rather than with free amines exposed by cleavage of the peptides from the DITC glass support. Thiol derivatised Tentagels are available from Rapp Polymere GmbH (Tübingen, Germany) or a thiol derivatised support can be prepared by incubating a silica gel with 3-mercaptopropyltrimethoxysilane.

In step 6 of this method the released peptides are recovered. If optional steps 3 and 5 are used the peptides may be present in a variety of solvents or buffers. These will be selected to be volatile in preferred embodiments. If the peptides are recovered directly from the first support, which is DITC glass in preferred embodiments, then it is likely that the peptides will be in TFA, which is volatile. The peptides are preferably recovered from these volatile solvents or buffers by evaporating the solvent or buffer. The peptides isolated by this method will have a free alpha-amino group available for reaction with the labels of this invention.

Labelling Isolated Peptides

Any of the mass labels of the present invention can be used in the protein expression profiling embodiments described in this aspect of the invention. The mass labels illustrated in FIGS. 22 and 23 are particularly preferred for use with this invention, especially this aspect of the present invention. These compounds have a vinyl sulphone reactive group, which will allow these compounds to undergo addition reactions with free amines and thiols. If only one label is desired per peptide then the proteins in the complex mixtures may be treated with capping agents prior to cleavage with the sequence specific endopeptidase. Phenyl, ethyl and methyl vinyl sulphone will react with free amines and thiols capping them while still permitting cleavage by trypsin of the capped proteins. The epsilon amine residues of lysine will react with two vinyl sulphone moieties if the vinyl sulphone moieties are not hindered, particularly ethyl and methyl vinyl sulphone.

After attachment of the markers these labelled peptides will have a mass that is shifted by the mass of the label. The mass of the peptide may be sufficient to identify the source protein. In this case only the label needs to be detected which can be achieved by selected reaction monitoring with a triple quadrupole, discussed in more detail below. Briefly, the first quadrupole of the triple quadrupole is set to let through ions whose mass-to-charge ratio corresponds to that of the peptide of interest, adjusted for the mass of the marker. The selected ions are then subjected to collision induced dissociation (CID) in the second quadrupole. Under the sort of conditions used in the analysis of peptides the ions will fragment mostly at the amide bonds in the molecule. The markers in FIGS. 22 and 23 have an amide bond, which releases the terminal pre-ionised portion of the tag on cleavage. Although the tags all have the same mass, the terminal portion is different because of differences in the substituents on either side of the amide bond. Thus the markers can be distinguished from each other. The presence of the marker fragment associated with an ion of a specific mass should confirm that the ion was a peptide and the relative peak heights of the tags from different samples will give information about the relative quantities of the peptides in their samples. If the mass is not sufficient to identify a peptide, either because a number of terminal peptides in the sample have the same terminal mass or because the peptide is not known, then sequence information maybe determined by analysis of the complete CID spectrum. FIG. 24 shows a theoretical spectrum for two samples of a peptide with the sequence H$_2$N-gly-leu-ala-ser-glu-COOH (SEQ ID NO: 1), where each sample is attached to one of the labels with the formulae shown in FIG. 23. The spectrum is idealised, as it only shows the b-series fragments and does not show other fragmentations or any noise peaks, however it does illustrate that the spectrum is clearly divided into a higher mass region corresponding to peptide fragmentation peaks and a lower mass region corresponding to mass label peaks. If desired, the peptide fragmentation peaks can be used to identify the peptides while the mass tag peaks give information about the relative quantities of the peptides.

Separation of Labelled Peptides by Chromatography or Electrophoresis

Preferably in this aspect of the invention, in the step prior to mass spectroscopic analysis the labelled terminal peptides are subjected to a chromatographic separation prior to analysis by mass spectrometry. This is preferably High Performance Liquid Chromatography (HPLC) which can be coupled directly to a mass spectrometer for in-line analysis of the peptides as they elute from the chromatographic column. A variety of separation techniques may be performed by HPLC but reverse phase chromatography is a popular method for the separation of peptides prior to mass spectrometry. Capillary zone electrophoresis is another separation method that may be coupled directly to a mass spectrometer for automatic analysis of eluting samples. These and other fractionation techniques may be applied to reduce the complexity of a mixture of peptides prior to analysis by mass spectrometry.

Protein Quantification and Identification by Tandem Mass Spectrometry

In the method of this aspect of the invention, the labelled isolated peptides are analysed by tandem mass spectrometry.

As discussed earlier tandem mass spectrometers allow ions with a pre-determined mass-to-charge ratio to be selected and fragmented, e.g. by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are usually denoted a$_n$, bn, c$_n$, etc. for cleavage at the n$^{th}$ peptide bond, where the charge of the ion is retained on the N-terminal fragment of the ion. Similarly, fragment series are denoted x$_n$, y$_n$, z$_n$, etc. where the charge is retained on the C-terminal fragment of the ion. This notation is depicted in the following Scheme 1:

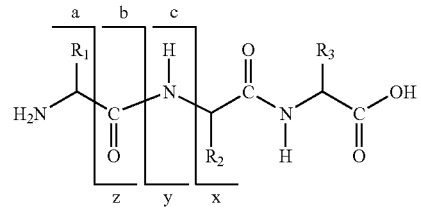

Scheme 1

Trypsin and thrombin are favoured cleavage agents for tandem mass spectrometry as they produce peptides with basic groups at both ends of the molecule, i.e. the alpha-amino group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the b-series.

If the isolated peptides used in the method of this invention are C-terminal peptides isolated using DITC glass as discussed above, the peptides will have a free amine after isolation at their N-termini facilitating labelling with the labels of this invention. As mentioned above, these labels may all have the same mass so equivalent peptides in each sample that is analysed will be shifted in mass by the same amount. CID of these peptides will produce fragments from the labels. The intensities of the label fragments will allow the relative quantities of equivalent peptides in each sample to be determined. Covalently linking the mass labels of this invention to the N-termini of the isolated peptides will shift the masses of the b-series of fragment ions by the mass of the label, as long as the charge remains on the label. Since the mass of the label used for each sample under analysis is the same, there will be only one ion series produced for all of the samples as long as collision induced scission of the labelled peptides takes place in the peptide backbone. This means that it is possible to identify the labelled peptides by their fragment ions and for any given peptide there will be only one fragment series for that peptide, irrespective of the number of samples being analysed simultaneously. Fragmentation within the labels themselves will produce peaks characteristic of each sample. These peaks will occur in a relatively low mass range (see FIG. 24). With a triple quadrupole instrument, it is preferable to use selected reaction monitoring to achieve the most sensitive detection of these peaks. The relative intensities of these peaks will be indicative of the relative amounts of the source protein, from which the peptide was derived, in the original samples. In natural peptides, the b-series of fragment ions tends to be of lower intensity than the y-series. With an appropriately basic mass label or a "pre-ionised" mass label, comprising for example a quaternary ammonium centre, the intensity of the b-series of ion fragments may be enhanced. Unfortunately, if C-terminal peptides are used there is no guarantee that the C-terminal amino acid will be basic, so the y-series fragment ions may be weak. Determination of structural information using the y-series would require that the C-terminus of these peptides carry a basic group or a "pre-ionised" group.

The analysis of proteins by tandem mass spectrometry, particularly mixtures of proteins, is complicated by the "noisiness" of the spectra obtained. Proteins isolated from biological samples are usually contaminated with buffering reagents, denaturants and detergents, all of which introduce peaks into the mass spectrum. As a result, there are often more contamination peaks in the spectrum than peptide peaks, and identifying peaks that correspond to peptides can be a major problem, especially with small samples of proteins that are difficult to isolate. As a result various methods are used to determine which peaks correspond to peptides before detailed CID analysis is performed. Triple quadrupole based instruments permit "precursor ion scanning" (see Wilm M. et al., Anal. Chem. 68(3) 527-33, "Parent ion scans of unsepa-rated peptide mixtures" (1996)). The triple quadrupole is operated in "single reaction monitoring" mode, in which the first quadrupole scans over the full mass range and each gated ion is subjected to CID in the second quadrupole. The third quadrupole is set to detect only one specific fragment ion, which is usually a characteristic fragment ion from a peptide such as ammonium ions. An alternative method used with quadrupole/time-of-flight mass spectrometers scans for doubly charged ions by identifying ions which when subjected to CID produce daughter ions with higher mass-to-charge ratios than the parent ion. A further method of identifying doubly charged ions is to look for sets of peaks in the spectrum which are only 0.5 daltons apart with appropriate intensity ratios which would indicate that the ions are the same differing only by the proportion of $^{13}C$ present in the molecule.

By labelling peptides with the mass labels of this invention, a novel form of precursor ion scanning may be envisaged in which peptide peaks are identified by the presence of fragments corresponding to the mass labels of this invention after subjecting the labelled peptides to CID. In particular, the peptides isolated from each sample by the methods of this invention may be labelled with more than one mass label. An equimolar mixture of a "precursor ion scanning" label which is used in all samples and a sample specific label may be used to label the peptides in each sample. In this way changes in the level of peptides in different samples will not have an adverse effect on the identification of peptide peaks in a precursor ion scan.

Having identified and selected a peptide ion, it is preferably subjected to CID. The CID spectra are often quite complex and determining which peaks in the CID spectrum correspond to meaningful peptide fragment series is a further problem in determining the sequence of a peptide by mass spectrometry. Shevchenko et al., Rapid Commun. Mass Spec. 11 1015-1024 (1997) describe a further method, which involves treating proteins for analysis with trypsin in 1:1 $^{16}O/^{18}O$ water. The hydrolysis reaction results in two populations of peptides, the first whose terminal carboxyl contains $^{16}O$ and the second whose terminal carboxyl contains $^{18}O$. Thus for each peptide in the sample there should be a double peak of equal intensity for each peptide where the double peak is 2 daltons apart. This is complicated slightly by intrinsic peptide isotope peaks but allows for automated scanning of the CID spectrum for doublets. The differences in mass between doublets can be determined to identify the amino acid by the two fragments differ. This method may be applicable with the methods of this invention if N-terminal peptides are isolated.

The invention claimed is:

1. A method of analysis, which method comprises detecting an analyte by identifying by mass spectrometry a mass label or a combination of mass labels relatable to the analyte, wherein the mass label is selected from:
   (a) a mass label from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
   (b) a mass label from an array comprising two or more sets of mass labels as defined in (a), wherein the aggregate mass of each of the mass labels of any one set in the array is different from the aggregate mass of each of the mass labels of every other set in the array.

2. A method according to claim 1, in which two or more analytes are detected by simultaneously identifying their mass labels or combinations of mass labels by mass spectrometry.

3. A method according to claim 1, wherein each analyte is identified by a unique combination of mass labels from a set or array of mass labels, each combination being distinguished by the presence and absence of each mass label in the set or array and/or the quantity of each mass label.

4. A method according to claim 1 for identifying two or more analytes, wherein the analytes are separated according to their mass, prior to detecting the mass label by mass spectrometry.

5. A method according to claim 4, wherein separation is carried out by a chromatographic or electrophoretic method.

6. A method according to claim 1, wherein a mass spectrometer is employed to detect the mass label, and wherein the mass spectrometer comprises one or more mass analysers, which mass analysers are capable of allowing ions of a particular mass, or range of masses, to pass through for detection and/or are capable of causing ions to dissociate.

7. A method according to claim 6, wherein ions of a particular mass or range of masses specific to one or more known mass labels are selected using the mass analyser, the selected ions are dissociated, and the dissociation products are detected to identify ion patterns indicative of the selected mass labels.

8. A method according to claim 6, wherein the mass spectrometer comprises three quadrupole mass analysers.

9. A method according to claim 7, wherein a first mass analyser is used to select ions of a particular mass or mass range, a second mass analyser is used to dissociate the selected ions, and a third mass analyser is used to detect resulting ions.

10. A method according to claim 1, which method comprises:
    (a) contacting one or more analytes with a set or array of probes selected from:
        (i) a set of two or more probes, each probe in the set being different and being attached to a unique mass label or a unique combination of mass labels, from the set of mass labels as defined in claim 1; or
        (ii) an array of probes comprising two or more sets of probes, wherein each probe in any one set is attached to a unique mass label, or a unique combination of mass labels, from the set of mass labels as defined in claim 1, and wherein the probes in any one set are attached to mass labels from the same set of mass labels, and each set of probes is attached to mass labels from unique sets of mass labels from the array of mass labels as defined in claim 1;
    (b) identifying an analyte, by detecting a probe relatable to that analyte.

11. A method according to claim 10, wherein the mass label is cleaved from the probe prior to detecting the mass label by mass spectrometry.

12. A method according to claim 10, which method comprises contacting one or more nucleic acids with a set of hybridisation probes.

13. A method according to claim 12, wherein the set of hybridization probes comprises a set of up to 256 4-mers, each probe in the set having a different combination of nucleic acid bases.

14. A method of two-dimensional mass spectrometric analysis, which method comprises:
    (a) providing one or more analytes, each analyte being labelled with a mass label or a combination of mass labels, wherein the mass labels are selected from:
        (i) mass labels from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
        (ii) mass labels from an array comprising two or more sets of mass labels as defined in (i), wherein the aggregate mass of each of the mass labels of any one set in the array is different from the aggregate mass of each of the mass labels of every other set in the array;
    (b) cleaving the mass labels from the analytes;
    (c) detecting the mass labels;
    (d) dissociating the mass labels in the mass spectrometer, to release the mass marker moieties from the mass normalisation moieties;
    (e) detecting the mass marker moieties; and
    (f) identifying the analytes on the basis of the mass spectrum of the mass labels and the mass spectrum of the mass marker moieties.

15. A method according to claim 14, wherein in step (c) mass labels of a chosen mass or a chosen range of masses are selected for detection, and/or in step (e) mass marker moieties having a specific mass or a specific range of masses are selected for detection.

16. A method of analysis, which method comprises:
    (a) subjecting a mixture of labelled analytes to a first separation treatment on the basis of a first property of the analytes;
    (b) subjecting the resulting separated analytes to a second separation treatment on the basis of a second property of the analytes; and
    (c) detecting an analyte by detecting its label; wherein the analytes are labelled with a mass label from a set or an array of mass labels selected from:
        (i) mass labels from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
        (ii) mass labels from an array comprising two or more sets of mass labels as defined in (i), wherein the aggregate mass of each of the mass labels of any one set in the array is different from the aggregate mass of each of the mass labels of every other set in the array.

17. A method according to claim 16 wherein in step (a) and/or step (b) the analytes are separated according to their length or mass.

18. A method according to claim 16, wherein in step (a) and/or step (b) the analytes are separated according to their iso-electric point.

19. A method according to claim 16, wherein the analytes comprise a protein, a polypeptide, a peptide an amino acid or a nucleic acid, or fragments thereof.

20. A method of claim 16, wherein the method comprises 2-dimensional gel electrophoresis.

21. A method for characterising a nucleic acid, which comprises:

(a) providing a population of nucleic acid fragments, each fragment having cleavably attached thereto a mass label selected from:
- a mass label from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
- (ii) a mass label from an array comprising two or more sets of mass labels as defined in (i), wherein the aggregate mass of each of the mass labels of any one set in the array is different from the aggregate mass of each of the mass labels of every other set in the array;

(b) separating the fragments on the basis of their length;
(c) cleaving each fragment to release its mass label; and
(d) determining each mass label by mass spectroscopy to relate the feature of each fragment to the length of the fragment.

22. A method according to claim 21 for characterizing cDNA, which method comprises:
(a) exposing a sample comprising a population of one or more cDNAs or fragments thereof to a cleavage agent which recognises a predetermined sequence and cuts at a reference site at a known displacement from the predetermined sequence proximal to an end of each cDNA or fragment thereof so as to generate a population of terminal fragments;
(b) ligating to each reference site an adaptor oligonucleotide which comprises a recognition site for a sampling cleavage agent;
(c) exposing the population of terminal fragments to a sampling cleavage agent which binds to the recognition site and cuts at a sampling site of known displacement from the recognition site so as to generate in each terminal fragment a sticky end sequence of a predetermined length of up to 6 bases, and of unknown sequence;
(d) separating the population of terminal fragments into sub-populations according to sequence length; and
(e) determining each sticky end sequence by:
(i) probing with an array of labelled hybridisation probes, the array containing all possible base sequences of the predetermined length;
(ii) ligating those probes which hybridise to the sticky end sequences; and
(iii) determining which probes are ligated by identification and preferably quantification of the labels;
wherein the labels are mass labels selected from:
(aa) a mass label from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
(bb) a mass label from an array comprising two or more sets of mass labels as defined in (aa), wherein the aggregate mass of each of the mass labels of any one set in the array is different from the aggregate mass of each of the mass labels of every other set in the array.

23. A method according to claim 22, wherein the population of terminal fragments is separated by capillary electrophoresis, HPLC or gel electrophoresis.

24. A method for characterising nucleic acid, which method comprises generating Sanger ladder nucleic acid fragments from one or more nucleic acid templates, in the presence of at least one labelled terminating base, and identifying the length of the fragment, and the terminating base of the fragment, wherein the label is relatable to the terminating base and is a mass label selected from:
(a) a mass label from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
(b) a mass label from an array comprising two or more sets of mass labels as defined in (a), wherein the aggregate mass of each of the mass labels of any one set in the array is different from the aggregate mass of each of the mass labels of every other set in the array.

25. A method according to claim 24, wherein all four terminating bases are present in the same reaction zone.

26. A method according to claim 24 or claim 25, which method comprises generating Sanger ladder nucleic acid fragments from a plurality of nucleic acid templates present in the same reaction zone, and for each nucleic acid fragment produced identifying the length of the fragment, the identity of the template from which the fragment is derived and the terminating base of the fragment, wherein prior to generating the fragments, a labelled primer nucleotide or oligonucleotide is hybridised to each template, the label on each primer being specific to the template to which that primer hybridises to allow identification of the template.

27. A method for sequencing nucleic acid, which method comprises:
(a) obtaining a target nucleic acid population comprising one or more single-stranded DNAs to be sequenced, each of which is present in a unique amount and bears a primer to provide a double-stranded portion of the nucleic acid for ligation thereto;
(b) contacting the nucleic acid population with an array of hybridization probes, each probe comprising a label cleavably attached to a known base sequence of predetermined length, the array containing all possible base sequences of that predetermined length and the base sequences being incapable of ligation to each other, wherein the contacting is carried out in the presence of ligase under conditions to ligate to the double-stranded portion of each nucleic acid the probe bearing the base sequence complementary to the single-stranded nucleic acid adjacent the double-stranded portion thereby to form an extended double-stranded portion which is incapable of ligation to further probes; and
(c) removing all unligated probes; followed by the steps of:

(d) cleaving the ligated probes to release each label;
(e) recording the quantity of each label by mass spectrometry; and
(f) activating the extended double-stranded portion to enable ligation thereto; wherein
(g) steps (b) to (f) are repeated in a cycle for a sufficient number of times to determine the sequence of the or each single-stranded nucleic acid by determining the sequence of release of each mass label, wherein the mass label is selected from:
  (i) a mass label from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
  (ii) a mass label from an array comprising two or more sets of mass labels as defined in (i), wherein the aggregate mass of each of the mass labels of any one set in the array is different from the aggregate mass of each of the mass labels of every other set in the array.

28. A method according to claim 27, wherein the hybridisation probes are a set of 256 4-mers, each probe in the set having a different combination of nucleic acid bases.

29. A method for characterising a sample comprising peptides, polypeptides and/or proteins, which method comprises:
  (a) providing a sample comprising peptides, polypeptides and/or proteins, each peptide, polypeptide and/or protein having cleavably attached thereto a mass label, or a combination of mass labels selected from:
    (i) mass labels from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
    (ii) mass labels from an array comprising two or more sets of mass labels as defined in (i), wherein the aggregate mass of each of the mass labels of any one set in the array is different from the aggregate mass of each of the mass labels of every other set in the array,
  wherein each peptide, polypeptide and/or protein is relatable to its label or combination of labels;
  (b) analysing the labelled peptides, polypeptides and/or proteins, by mass spectrometry to detect the labels.

30. A method according to claim 29, wherein the sample is provided by forming peptides from the action of a cleavage agent on a sample comprising polypeptides and/or proteins.

31. A method according to claim 29 or claim 30, wherein the labelled peptides, polypeptides and/or proteins are separated by a chromatographic or electrophoretic method, prior to analysing.

32. A method according to claim 29, wherein a plurality of samples is provided.

33. A method according to claim 32, wherein the plurality of samples is pooled, prior to analysis.

34. A method according to claim 29, wherein one or more of the peptides, polypeptides and/or proteins in the sample is post-translationally modified and comprises a carbohydrate, and wherein the method comprises biotinylating the modified peptide, polypeptide or protein by attaching biotin via a carbonyl group of the carbohydrate.

35. A method according to claim 29, wherein one or more of the peptides, polypeptides and/or proteins in the sample is post-translationally modified by tyrosine phosphorylation, and wherein the method comprises separating such modified peptides, polypeptides and/or proteins by affinity chromatography using an anti-phosphotyrosine antibody.

36. A method according to claim 29, which method comprises isolating a single peptide fragment from each peptide, polypeptide and/or protein.

37. A method according to claim 36, wherein each isolated fragment is a terminal fragment.

38. A method according to claim 37, which method comprises:
  (a) treating a sample comprising a population of a plurality of polypeptides with a cleavage agent which is known to recognise in polypeptide chains a specific amino acid residue or sequence and to cleave at a cleavage site, whereby the population is cleaved to generate peptide fragments;
  (b) isolating a population of peptide fragments bearing as a reference terminus the N-terminus or the C-terminus of the polypeptide from which they were fragmented, each peptide fragment bearing at the other end the cleavage site proximal to the reference terminus;
  (c) prior to or after isolating the peptide fragments, labelling each reference terminus of the polypeptides with a mass label, or a combination of mass labels selected from:
    (i) mass labels from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
    (ii) mass labels from an array comprising two or more sets of mass labels as defined in (i), wherein the aggregate mass of each of the mass labels of any one set in the array is different from the aggregate mass of each of the mass labels of every other set in the array, wherein each reference terminus is relatable to its label or combination of labels; and
  (d) determining by mass spectrometry a signature sequence of one or more of the isolated fragments, which signature sequence is the sequence of a pre-determined number of amino acid residues running from the cleavage site; wherein a signature sequence characterises each polypeptide.

39. A method according to claim 37, which method comprises:
  (a) contacting a sample comprising one or more polypeptides with a first cleavage agent to generate polypeptide fragments;

(b) isolating one or more polypeptide fragments, each fragment comprising the N-terminus or the C-terminus of the polypeptide from which it was fragmented;

(c) prior to or after isolating the polypeptide fragments, labelling each terminus of the polypeptides with a mass label, or a combination of mass labels selected from:

(i) mass labels from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or (ii) mass labels from an array comprising two or more sets of mass labels as defined in (i), wherein the aggregate mass of each of the mass labels of any one set in the array is different from the aggregate mass of each of the mass labels of every other set in the array, wherein each terminus is relatable to its label or combination of labels; and (d) identifying the isolated fragments by mass spectrometry;

(e) repeating steps (a)-(d) on the sample using a second cleavage agent that cleaves at a different site from the first cleavage agent; and (f) characterising the one or more polypeptides in the sample from the fragments identified in steps (d) and (e).

40. A method according to claim 1, in which each mass marker moiety in the set has the same structural core, and each mass normalisation moiety in the set has the same structural core that may be the same or different from the structural core of the mass marker moieties, and wherein each mass label in the set comprises one or more mass adjuster moieties, the mass adjuster moieties being attached to or situated within the structural core of the mass marker moiety and/or the structural core of the mass normalisation moiety, such that every mass marker moiety in the set comprises a different number of mass adjuster moieties and every mass label in the set has the same number of mass adjuster moieties.

41. A method according to claim 40, wherein each mass label in the set comprises the following structure:

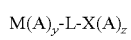

wherein M is a mass normalisation moiety, X is a mass marker moiety, A is a mass adjuster moiety, L is a cleavable linker, y and z are integers of 0 or greater, and y+z is an integer of 1 or greater.

42. A method according to claim 40, wherein the mass adjuster moiety is selected from:

(a) an isotopic substituent situated within the structural core of the mass marker moiety and/or within the structural core of the mass normalisation moiety, and (b) substituent atoms or groups attached to the structural core of the mass marker moiety and/or attached to the structural core of the mass normalisation moiety.

43. A method according to claim 42, wherein the mass adjuster moiety is selected from a halogen atom substituent, a methyl group and $^2H$ or $^{13}C$ isotopic substituents.

44. A method according to claim 43, wherein the mass adjuster moiety is a fluorine atom substituent.

45. A method according to claim 1, wherein the cleavable linker attaching the mass marker moiety to the mass normalisation moiety is a linker cleavable by collision.

46. A method according to claim 45, wherein the cleavable linker comprises an amide bond.

47. A method according to claim 1, wherein the mass normalisation moiety comprises a fragmentation resistant group.

48. A method according to claim 47, wherein the mass normalisation moiety comprises a phenyl group.

49. A method according to claim 1, wherein the mass marker moiety comprises a pre-ionised group.

50. A method according to claim 49, wherein the mass marker moiety comprises an N-methyl pyridyl group, or a group selected from the following groups: $-NH_2$, $-NR_2$, $-NR_3^+$, $-SR_3^+$, $-SO_3^-$, $-PO_4^-$, $-PO_3^-$, $-CO_2^-$,

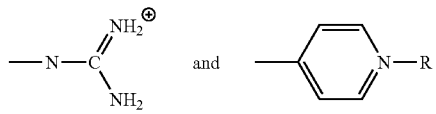

wherein R is hydrogen or is a substituted or unsubstituted aliphatic, aromatic, cyclic or heterocyclic group.

51. A method according to claim 41, wherein each of the labels in the set has the following structure:

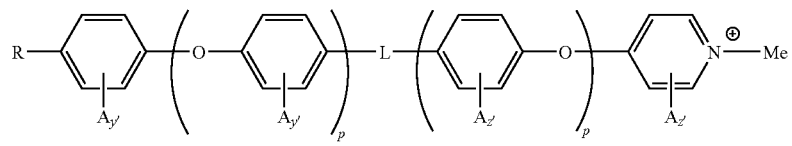

wherein R is hydrogen or is a substituted or unsubstituted aliphatic, aromatic, cyclic or heterocyclic group; L is a cleavable linker; A is a mass adjuster moiety; each p is the same and is an integer of 0 or greater; each y' may be the same or different and is an integer of 0-4, the sum of all y' for any one label being equal to y; each z' may be the same or different and is an integer of 0-4, the sum of all z' for any one lapel being equal to z; and y+z is an integer of 1 or greater.

52. A method according to claim 51, wherein R is H, L is an amide bond, p=0, and A is an F atom.

53. A method according to claim 1, wherein each mass label in at least one set in the array as defined in claim 34, part (b), comprises a mass series modifying group of the same mass as determined by mass spectrometry, the mass series modifying group in each of the mass labels of any one set having a different mass from the mass series modifying groups in each of the mass labels of every other set in the array.

54. A method according to claim 53, wherein the mass series modifying groups are attached to the mass labels such that, upon cleaving the cleavable linker of the mass labels, the mass series modifying groups become detached from the mass marker moieties.

55. A method according to claim 53, wherein the mass series modifying groups of each set in the array have the same structural core, and each mass label of any one set in the array has the same number of mass series modifying groups as the other mass labels of that set, and a different number of mass series modifying groups from the mass labels of every other set in the array.

56. A method according to claim 55, each mass label in the array having either of the following structures:

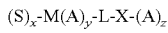

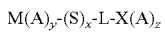

wherein S is a mass series modifying group; M is a mass normalisation moiety; X is a mass marker moiety; A is a mass adjuster moiety; L is a cleavable linker; x is an integer of 0 or greater; y and z are integers of 0 or greater; and y+z is an integer of 1 or greater.

57. A method according to claim 53, wherein the mass series modifying groups comprise an aryl ether group.

58. A method according to claim 56, each mass label in the array having either of the following structures:

59. A method according to claim 53, wherein the mass series modifying groups of every set in the array have the same structural core, the mass series modifying group of the mass labels of at least one set comprising one or more mass adjuster moieties, the mass adjuster moieties being attached to or situated within the structural core of the mass series modifying group.

60. A method according to claim 59, in which every mass label of every set in the array has the same number of mass series modifying groups, wherein the mass series modifying group in each mass label of any one set has the same number of mass adjuster moieties as the mass series modifying groups in every other label of that set, and wherein the mass series modifying groups in the mass labels of any one set have a different number of mass adjuster moieties from the mass series modifying groups in the labels of every other set in the array.

61. A method according to claim 60, wherein each of the sets in the array comprises mass labels having either of the following structures:

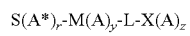

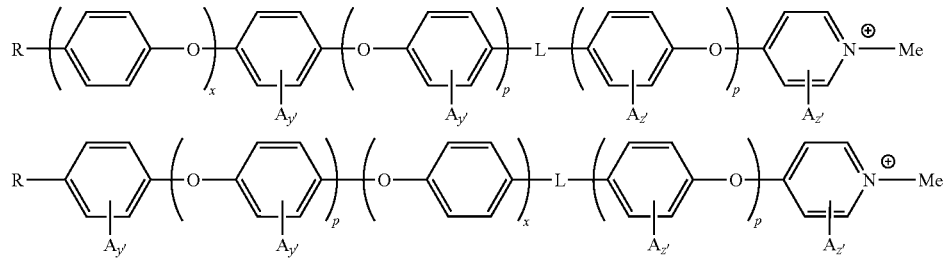

wherein A is a mass adjuster moiety; L is a cleavable linker; y and z are integers of 0 or greater; R is hydrogen or is a substituted or unsubstituted aliphatic, aromatic, cyclic or heterocyclic group; each p is the same and is an integer of 0 or greater; x is an integer of 0 or greater, x being the same for each mass label in any one set of the array, and the x of any one set being different from the x of every other set in the array; each y' may be the same or different and is an integer of 0-4, the sum of all y' for any one label being equal to y, and each z' may be the same or different and is an integer of 0-4, the sum of all z' for any one label being equal to z; and y+z is an integer of 1 or greater.

wherein S is a mass series modifying group; M is a mass normalisation moiety; X is a mass marker moiety; A is a mass adjuster moiety of the mass marker moieties and mass normalisation moieties; A* may be the same or different from A and is a mass adjuster moiety of the mass series modifying groups; L is a cleavable linker; r is an integer of 0 or greater and is at least 1 for one or more sets of mass labels in the array; y and z are integers of 0 or greater; and y+z is an integer of 1 or greater.

62. A method according to claim 61, wherein each of the sets in the array comprises mass labels having either of the following structures:

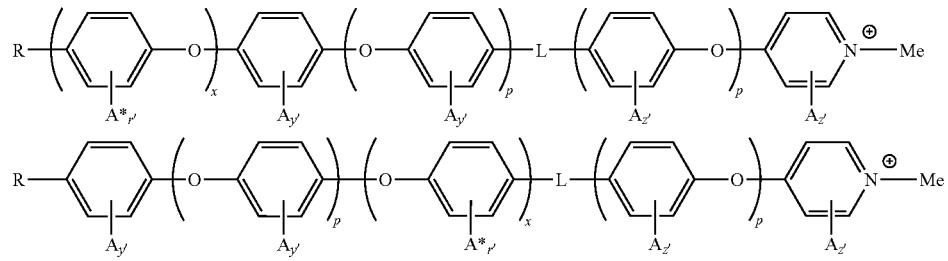

wherein A is a mass adjuster moiety; L is a cleavable linker; y and z are integers of 0 or greater; wherein R is hydrogen or is a substituted or unsubstituted aliphatic, aromatic, cyclic or heterocyclic group; each p is the same and is an integer of 0 or greater; x is an integer of 0 or greater x being the same for all mass labels in the array; each y' may be the same or different and is an integer of 0-4, the sum of all y' for any one label being equal to y; each z' may be the same or different and is an integer of 0-4, the sum of all z' for any one label being equal to z; y+z is an integer of 1 or greater; each r' may be the same or different, the sum of all r' for any one label being equal to r; and r is an integer of 0 or greater and is at least 1 for one or more sets of mass labels in the array.

63. A method according to claim 1, wherein the mass labels of any one set in the array as defined in claim 34, part (b), differ in mass from the mass labels of every other set in the array by 4 daltons or more.

64. A method according to claim 10, wherein each probe is attached to a unique combination of mass labels, each combination being distinguished by the presence and absence of each mass label in the set of mass labels and/or the quantity of each mass label attached to the probe.

65. A method according to claim 10, wherein each probe comprises a biomolecule.

66. A method according to claim 65, wherein the biomolecule is selected from a DNA, an RNA, an oligonucleotide, a nucleic acid base, a protein and/or an amino acid.

67. A set of two or more probes, each probe in the set being different and being attached to a unique mass label or a unique combination of mass labels selected from:
   (a) mass labels from a set of two or more mass labels, each mass label in the set comprising a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry; or
   (b) mass labels from an array comprising two or more sets of mass labels as defined in (a), wherein the aggregate mass of each of the mass labels of any one set in the array is different from the aggregate mass of each of the mass labels of every other set in the array.

68. An array of probes comprising two or more sets of probes, wherein each probe in any one set is attached to a unique mass label, or a unique combination of mass labels, from a set of mass labels wherein each mass label in the set comprises:
   a mass marker moiety attached via a cleavable linker to a mass normalisation moiety, the mass marker moiety being fragmentation resistant, wherein each mass normalisation moiety ensures that each mass label in the set has the same aggregate mass as determined by mass spectrometry, and wherein each mass marker moiety has a mass different from that of all other mass marker moieties as determined by mass spectrometry, and wherein all the mass labels in the set are distinguishable from each other by mass spectrometry,
   and wherein the probes in any one set are attached to mass labels from the same set of mass labels, and each set of probes is attached to mass labels from unique sets of mass labels from an array of mass labels comprising two or more sets of mass labels, wherein the aggregate mass of each of the mass labels of any one set in the array is different from the aggregate mass of each of the mass labels of every other set in the array.

69. A set or array of probes according to claim 67 or claim 68, wherein each probe is attached to a unique combination of mass labels, each combination being distinguished by the presence and absence of each mass label in the set of mass labels and/or the quantity of each mass label attached to the probe.

70. A set or array of probes according to claim 67, wherein each probe comprises a biomolecule.

71. A set or array of probes according to claim 70, wherein the biomolecule is selected from a DNA, an RNA, an oligonucleotide, a nucleic acid base, a protein and/or an amino acid.

* * * * *

```
                       SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      Illustrative peptide

<400> SEQUENCE: 1

Gly Leu Ala Ser Glu
 1               5
```